US012768826B2

(12) United States Patent
Singleton

(10) Patent No.: US 12,768,826 B2
(45) Date of Patent: Oct. 20, 2026

(54) BEVERAGE FLAVORING CONTROL SYSTEM

(71) Applicant: Christopher Singleton, Louisville, KY (US)

(72) Inventor: Christopher Singleton, Louisville, KY (US)

(73) Assignee: Christopher Singleton, Louisville, KY (US)

( * ) Notice: Subject to any disclaimer, the term of this patent is extended or adjusted under 35 U.S.C. 154(b) by 469 days.

(21) Appl. No.: 18/396,830

(22) Filed: Dec. 27, 2023

(65) Prior Publication Data

US 2025/0216372 A1 Jul. 3, 2025

(51) Int. Cl.

| | |
|---|---|
| ***G01N 33/14*** | (2006.01) |
| ***C12G 3/07*** | (2006.01) |
| ***C12H 1/22*** | (2006.01) |
| ***G01N 21/27*** | (2006.01) |

(52) U.S. Cl.

CPC ............. *G01N 33/146* (2013.01); *C12G 3/07* (2019.02); *C12H 1/22* (2013.01); *G01N 21/27* (2013.01)

(58) Field of Classification Search

CPC .................................................... G01N 33/146

See application file for complete search history.

(56) References Cited

U.S. PATENT DOCUMENTS

| | | | | | |
|---|---|---|---|---|---|
| 1,149,700 | A * | 8/1915 | Stitzel | A23L 2/52 | 426/598 |
| 1,464,520 | A * | 8/1923 | Von Horst | C12C 3/00 | 426/429 |
| 2,007,727 | A * | 7/1935 | Putt | A23L 27/11 | 426/429 |
| 2,786,766 | A * | 3/1957 | Meusel | A23L 27/70 | 426/310 |
| 2,899,313 | A * | 8/1959 | Makower et al. | A23L 27/70 | 426/321 |
| 2,926,090 | A * | 2/1960 | Williams | A23L 13/74 | 426/56 |
| 2,928,740 | A * | 3/1960 | Rosenthal | A23J 3/20 | 426/62 |
| 2,952,546 | A * | 9/1960 | Fonyo | C12C 5/026 | 426/546 |

(Continued)

*Primary Examiner* — David E Choi

(74) *Attorney, Agent, or Firm* — McGuire Woods LLP

(57) ABSTRACT

A method of training a machine learning model for evaluating flavor profiles of an alcoholic beverage includes a spectral sensor collecting optical properties of the beverage or flavoring agent suspended in the beverage within a container. Temperature and pressure sensors collect environment data of the container during a flavoring session. A control apparatus displays a user interface requesting a taste tester to select labels for the session. A control apparatus memory stores selected labels responsive to the taste tester's selections. A feature extraction module extracts features from the optical properties and environment data based on predetermined criteria. A machine learning engine trains a machine learning model to continuously learn flavor characteristics under a plurality of flavoring sessions using the extracted features and selected labels. The trained machine learning model is deployed for quality control and for determining the difference between a good batch and poor batch of the alcoholic beverage.

15 Claims, 17 Drawing Sheets

(56) References Cited

U.S. PATENT DOCUMENTS

| | | | | | |
|---|---|---|---|---|---|
| 3,056,679 | A * | 10/1962 | Williams | A23L 13/74 | 426/56 |
| 3,102,033 | A * | 8/1963 | Jackel | A23L 27/24 | 426/653 |
| 3,222,187 | A * | 12/1965 | Winter | A23L 27/2024 | 426/538 |
| 3,332,779 | A * | 7/1967 | Krabbe | C12G 3/021 | 426/16 |
| 3,397,062 | A * | 8/1968 | Nessly | A23L 5/00 | 426/650 |
| 3,449,128 | A * | 6/1969 | Komota | C12F 3/04 | 426/11 |
| 3,552,297 | A * | 1/1971 | Williams | F25D 17/06 | 62/157 |
| 3,645,753 | A * | 2/1972 | Gasser | A23L 27/215 | 426/655 |
| 3,713,838 | A * | 1/1973 | Ziegler | C12F 3/08 | 426/429 |
| 3,881,022 | A * | 4/1975 | Gasser | A23L 33/145 | 426/60 |
| 4,178,389 | A * | 12/1979 | Pilla | C12G 3/024 | 426/11 |
| 4,303,680 | A * | 12/1981 | Tanekawa | A23L 33/145 | 435/270 |
| 4,784,859 | A * | 11/1988 | Lashley | C12G 3/021 | 426/11 |
| 4,874,625 | A * | 10/1989 | Hartman | A23L 27/215 | 426/520 |
| 4,929,452 | A * | 5/1990 | Hamdy | C12M 23/34 | 426/11 |
| 5,626,894 | A * | 5/1997 | Bengtsson | A23L 27/23 | 426/11 |
| 5,922,389 | A * | 7/1999 | Steele | C12G 3/07 | 99/277.1 |
| 6,203,836 | B1 * | 3/2001 | Gross, II | A23L 27/201 | 426/489 |
| 6,242,039 | B1 * | 6/2001 | Bodett | A23L 15/00 | 426/651 |
| 6,495,184 | B1 * | 12/2002 | Zheng | A23L 27/215 | 426/534 |
| 6,767,571 | B2 * | 7/2004 | Rodger | A23L 5/00 | 426/62 |
| 7,556,833 | B2 * | 7/2009 | Dias | A23C 19/0328 | 426/534 |
| 9,848,627 | B2 * | 12/2017 | Ito | C12C 5/026 | |
| 10,925,303 | B2 * | 2/2021 | Kaji | A23L 27/105 | |
| 2002/0076475 | A1 * | 6/2002 | Gimbel | C12C 3/10 | 426/16 |
| 2002/0122861 | A1 * | 9/2002 | Tocantins | A23B 70/30 | 426/548 |
| 2004/0241280 | A1 * | 12/2004 | Saladino | A23G 9/045 | 426/11 |
| 2005/0042343 | A1 * | 2/2005 | Vickers | C12G 3/06 | 426/330 |
| 2005/0064066 | A1 * | 3/2005 | Ramsden | C12H 1/0408 | 426/11 |
| 2007/0048404 | A1 * | 3/2007 | Dias | A23L 27/25 | 426/43 |
| 2009/0022869 | A1 * | 1/2009 | Chakir | A23L 2/54 | 426/569 |
| 2009/0196951 | A1 * | 8/2009 | Brandborg | C12G 3/06 | 426/519 |
| 2010/0255163 | A1 * | 10/2010 | Anand | A23L 27/00 | 426/281 |
| 2011/0217420 | A1 * | 9/2011 | Lerner | A23F 3/40 | 426/597 |
| 2014/0154354 | A1 * | 6/2014 | Schiefen | C12G 3/02 | 426/16 |
| 2014/0170295 | A1 * | 6/2014 | Kaneko | A23L 11/65 | 426/598 |
| 2014/0314935 | A1 * | 10/2014 | Ward | A23C 21/06 | 426/583 |
| 2016/0289619 | A1 * | 10/2016 | Mancosky | B01F 27/2722 | |
| 2017/0238582 | A1 * | 8/2017 | Garnett | A23L 2/382 | |
| 2020/0245647 | A1 * | 8/2020 | Kalis | A23L 2/54 | |
| 2020/0270553 | A1 * | 8/2020 | Hall | C12G 3/07 | |
| 2022/0338508 | A1 * | 10/2022 | Wade | A23L 2/38 | |
| 2023/0082900 | A1 * | 3/2023 | Weideman | C12H 1/22 | 99/277.1 |
| 2024/0052279 | A1 * | 2/2024 | Wu, Jr. | C12G 1/00 | |
| 2024/0309302 | A1 * | 9/2024 | Gardner | A23C 9/156 | |
| 2025/0215365 | A1 * | 7/2025 | Singleton | G05D 23/1917 | |
| 2025/0263643 | A1 * | 8/2025 | Kreusch | C12G 3/07 | |

* cited by examiner

BEVERAGE FLAVORING CONTROL SYSTEM

FIELD OF THE INVENTION

The disclosure relates generally to beverage flavoring, and more particularly, to methods and systems for controlling the flavoring of an alcoholic beverage.

BACKGROUND

Beverages, specifically alcoholic beverages, are very popular among the world population. In many instances of creating an alcohol, a flavoring process is carried out that gives specific alcohols their unique flavor. Generally, this process takes years for certain alcoholic beverage to attain its distinct flavor. A prime example of an alcoholic beverage that utilizes this process is whiskey, which a lot of times is recognized by its "age" (5 year, 10 year, 20 year, etc.). In most of these processes, there is a lack of environmental parameter control during the lengthy process.

BRIEF DESCRIPTION OF THE DRAWINGS

For a more complete understanding of the features and advantages of the present disclosure, reference is now made to the detailed description along with the accompanying figures in which corresponding numerals in the different figures refer to corresponding parts and in which.

Figure 1A:
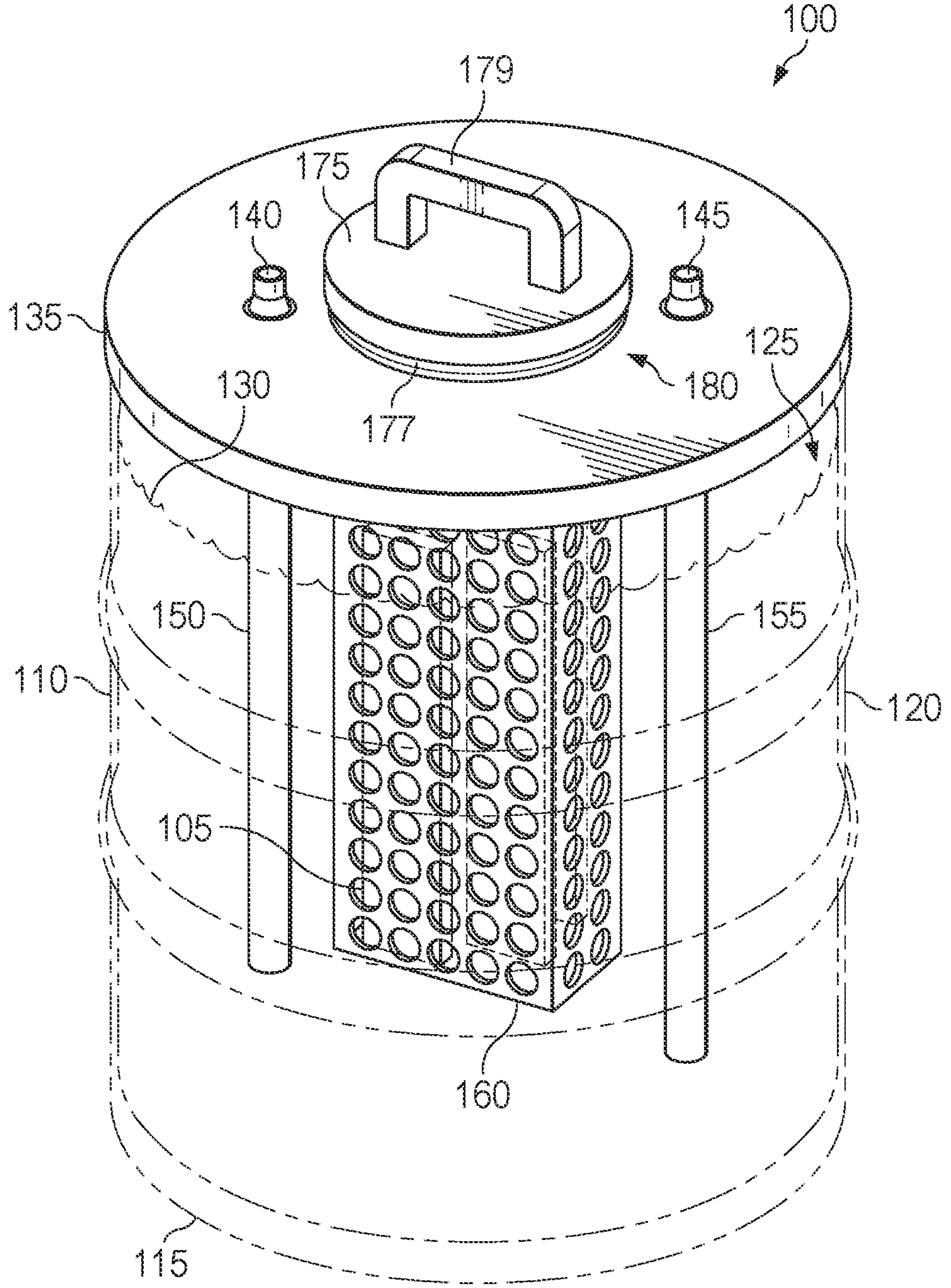
FIG. 1A is an illustration of a perspective view of a beverage flavoring container including a retaining device affixed to a lid section of the beverage flavoring container in accordance with certain embodiments of the present disclosure.

The illustrated figures are only exemplary and are not intended to assert or imply any limitation with regard to the environment, architecture, design, or process in which different examples may be implemented.

DETAILED DESCRIPTION

The disclosure relates generally to beverage flavoring, and more particularly, to methods and systems for controlling the flavoring of an alcoholic beverage. The term "beverage" is used herein to describe any liquid that is intended for human consumption. In multiple embodiments herein, the term "beverage" refers to an alcoholic beverage. The term "flavoring agent" is used herein to describe any substance capable of releasing molecules when suspended in a beverage over a period of time for the purposes of adding flavor to a beverage. The term "flavoring session" is used herein to describe a time period during which an alcoholic beverage is flavored within a container. The term "retaining device" is used herein to describe a device with an interior volume that is utilized to hold and at least partially suspend a flavoring agent in an alcoholic beverage.

While the making and using of various embodiments of the present disclosure are discussed in detail below, it should be appreciated that the present disclosure provides many applicable inventive concepts, which can be embodied in a wide variety of specific contexts. The specific embodiments discussed herein are merely illustrative and do not delimit the scope of the present disclosure. In the interest of clarity, not all features of an actual implementation may be described in the present disclosure.

Presented herein is a computer-implemented method of training a machine learning model for evaluating flavor profiles of an alcoholic beverage. The method comprises, for each of a plurality of flavoring sessions, collecting, via a spectral sensor, optical properties of at least one of the alcoholic beverage within a container or at least one flavoring agent suspended in the alcoholic beverage. At least one of a temperature sensor or a pressure sensor collects environment data of the beverage flavoring container during the flavoring session. Upon completion of the flavoring session, a control apparatus displays a user interface requesting a human taste tester to select a label (indicating a poor taste, a fair taste, or a good taste) for the completed flavoring session, where the human taste tester selects the label using the user interface. A memory of the control apparatus stores the selected label responsive to the selection of the human taste tester. A feature extraction module extracts features from the optical properties and the environment data based on predetermined criteria, where the extracted features including some of the optical properties and some of the environment data collected at different points in time during the flavoring session. A machine learning engine trains a machine learning model to continuously learn flavor characteristics under the plurality of flavoring sessions using the extracted features and the one or more labels selected by the human taste tester for the plurality of flavoring sessions, where the trained machine learning model is deployed for quality control of the alcoholic beverage and for determining the difference between a good batch of the alcoholic beverage and a poor batch of the alcoholic beverage.

Additionally presented herein is a system for training a machine learning model for evaluating flavor profiles of an alcoholic beverage. The system comprises a processor and a memory coupled to the processor to store instructions. The instructions, when executed by the processor, cause the processor to perform operations, where the operations include, for each of a plurality of flavoring sessions, collecting, via a spectral sensor, optical properties of at least one of the alcoholic beverage within a container or at least one flavoring agent suspended in the alcoholic beverage. At least one of a temperature sensor or a pressure sensor collects environment data of the beverage flavoring container during the flavoring session. Upon completion of the flavoring session, a control apparatus displays a user interface requesting a human taste tester to select a label (indicating a poor taste, a fair taste, or a good taste) for the completed flavoring session, where the human taste tester selects the label using the user interface. A memory of the control apparatus stores the selected label responsive to the selection of the human taste tester. A feature extraction module extracts features from the optical properties and the environment data based on predetermined criteria, where the extracted features including some of the optical properties and some of the environment data collected at different points in time during the flavoring session. A machine learning engine trains a machine learning model to continuously learn flavor characteristics under the plurality of flavoring sessions using the extracted features and the one or more labels selected by the human taste tester for the plurality of flavoring sessions, where the trained machine learning model is deployed for quality control of the alcoholic beverage and for determining the difference between a good batch of the alcoholic beverage and a poor batch of the alcoholic beverage.

Additionally presented herein is a computer program product for training a machine learning model for evaluating flavor profiles of an alcoholic beverage. The computer program product comprises a computer readable storage medium having program instructions embodied therewith, where the program instructions are executable by a processor to cause the processor to perform, for each of a plurality of flavoring sessions, collecting, via a spectral sensor, optical properties of at least one of the alcoholic beverage within a container or at least one flavoring agent suspended in the alcoholic beverage. At least one of a temperature sensor or a pressure sensor collects environment data of the beverage flavoring container during the flavoring session. Upon completion of the flavoring session, a control apparatus displays a user interface requesting a human taste tester to select a label (indicating a poor taste, a fair taste, or a good taste) for the completed flavoring session, where the human taste tester selects the label using the user interface. A memory of the control apparatus stores the selected label responsive to the selection of the human taste tester. A feature extraction module extracts features from the optical properties and the environment data based on predetermined criteria, where the extracted features including some of the optical properties and some of the environment data collected at different points in time during the flavoring session. A machine learning engine trains a machine learning model to continuously learn flavor characteristics under the plurality of flavoring sessions using the extracted features and the one or more labels selected by the human taste tester for the plurality of flavoring sessions, where the trained machine learning model is deployed for quality control of the alcoholic beverage and for determining the difference between a good batch of the alcoholic beverage and a poor batch of the alcoholic beverage.

FIG. 1A illustrates a perspective view of a beverage flavoring container 100 including a retaining device 160 affixed to a lid section 135 of the beverage flavoring container 100 in accordance with certain embodiments of the present disclosure. In the depicted embodiment, a body 110 of beverage flavoring container 100 includes a bottom section 115 and a sidewall section 120 disposed about a perimeter of the bottom section 115. An interior volume 125 of beverage flavoring container 100 contained within body 110 is filled with an alcoholic beverage 130. As shown, beverage flavoring container 100 is configured to receive one or more flavoring agents 105 (as depicted, pieces of wood) that are suspended within the alcoholic beverage 130 via retaining device 160. Once the alcoholic beverage 130 receives the flavoring agents 105, the process of flavoring the alcoholic beverage 130 begins. As further shown, a lid section 135 is affixed to the top side of sidewall section 120, enclosing the flavoring agents 105 and the alcoholic beverage 130 within beverage flavoring container 100.

In order to add and remove volume of the alcoholic beverage 130 to and from beverage flavoring container 100, an inlet orifice 140 and an outlet orifice 145 are positioned on lid section 135. Inlet orifice 140 includes an inlet tubing 150 being disposed about a perimeter of the inlet orifice 140 and extending into the interior volume 125 of beverage flavoring container 100 from inlet orifice 140, while outlet orifice 145 includes an outlet tubing 155 being disposed about a perimeter of the outlet orifice 145 and extending into the interior volume 125 of beverage flavoring container 100 from outlet orifice 145.

Additionally, in this embodiment, a retaining device 160 is integrated with a bottom portion of lid section 135 so that retaining device 160 is suspended within an alcoholic beverage 130 when lid section 135 is affixed to beverage flavoring container 100. A cover portion 175 removably attached to lid section 135 is disposed adjacent an attachment region 180 of retaining device 160 to lid section 135. Once cover portion 175 is removed from lid section 135, flavoring agents 105 may be added and/or removed from retaining device 160. In an embodiment, lid section 135 may include multiple retaining devices 160 and multiple cover portions 175 configured as described above. In additional embodiments, retaining device 160 is affixed to cover portion 175 and is removable from beverage flavoring container 100 along with cover portion 175.

In the embodiment shown, a decoupling mechanism to detach cover portion 175 from lid section 135 includes a twist-lock mechanism including male-female threading 177 and an engageable grip section 179 (handle). In order to disengage the threads 177, the grip section 179 integrated into lid section 135 is engaged by a hand of an individual and rotated until the threads 177 disengage. In additional embodiments, the decoupling mechanism to detach cover portion 175 from lid section 135 includes any of: a twist-lock mechanism, clips, a push-button disengagement mechanism, threading, a barrel ring (ring compression mechanism), or a tri-clamp.

Figure 1B:
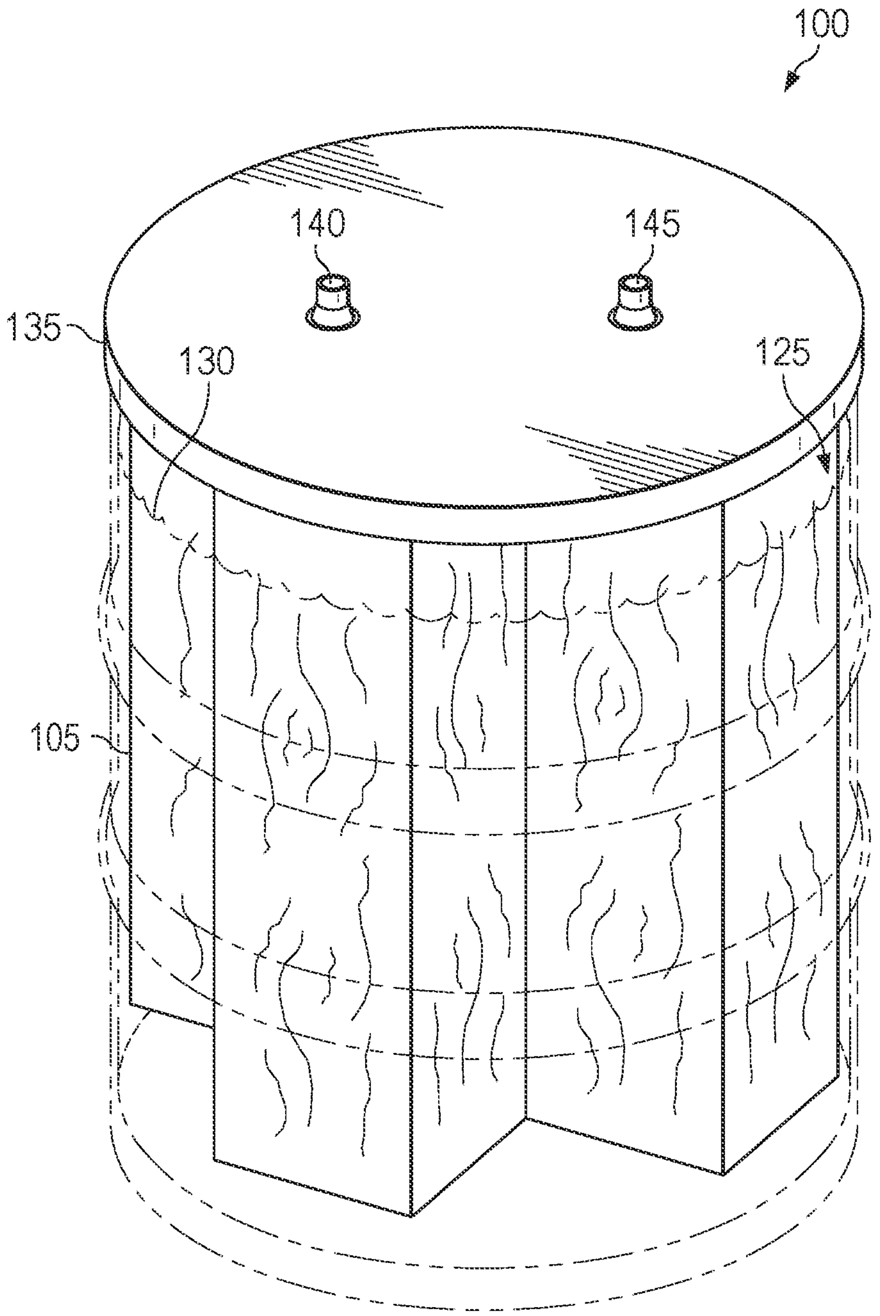
FIG. 1B is an illustration of a perspective view of a beverage flavoring container including a flavoring agent affixed to a lid section of the beverage flavoring container in accordance with certain embodiments of the present disclosure.

FIG. 1B illustrates a perspective view of a beverage flavoring container 100 including a flavoring agent 105 affixed to a lid section 135 of the beverage flavoring container 100 in accordance with certain embodiments of the present disclosure. Beverage flavoring container 100 is substantially similar to beverage flavoring container 100 of FIG. 1A; however, the retaining device 160 of FIG. 1A has been substituted with a flavoring agent 105 that is affixed to lid section 135. In an embodiment, each of the at least one flavoring agent 105 comprises a piece of wood or a wood structure. In additional embodiments, each of the at least one piece of wood comprises a lattice configuration, where the lattice configuration is configured to increase surface area exposure of each of the at least one flavoring agent 105 to the alcoholic beverage 130.

Figure 1C:
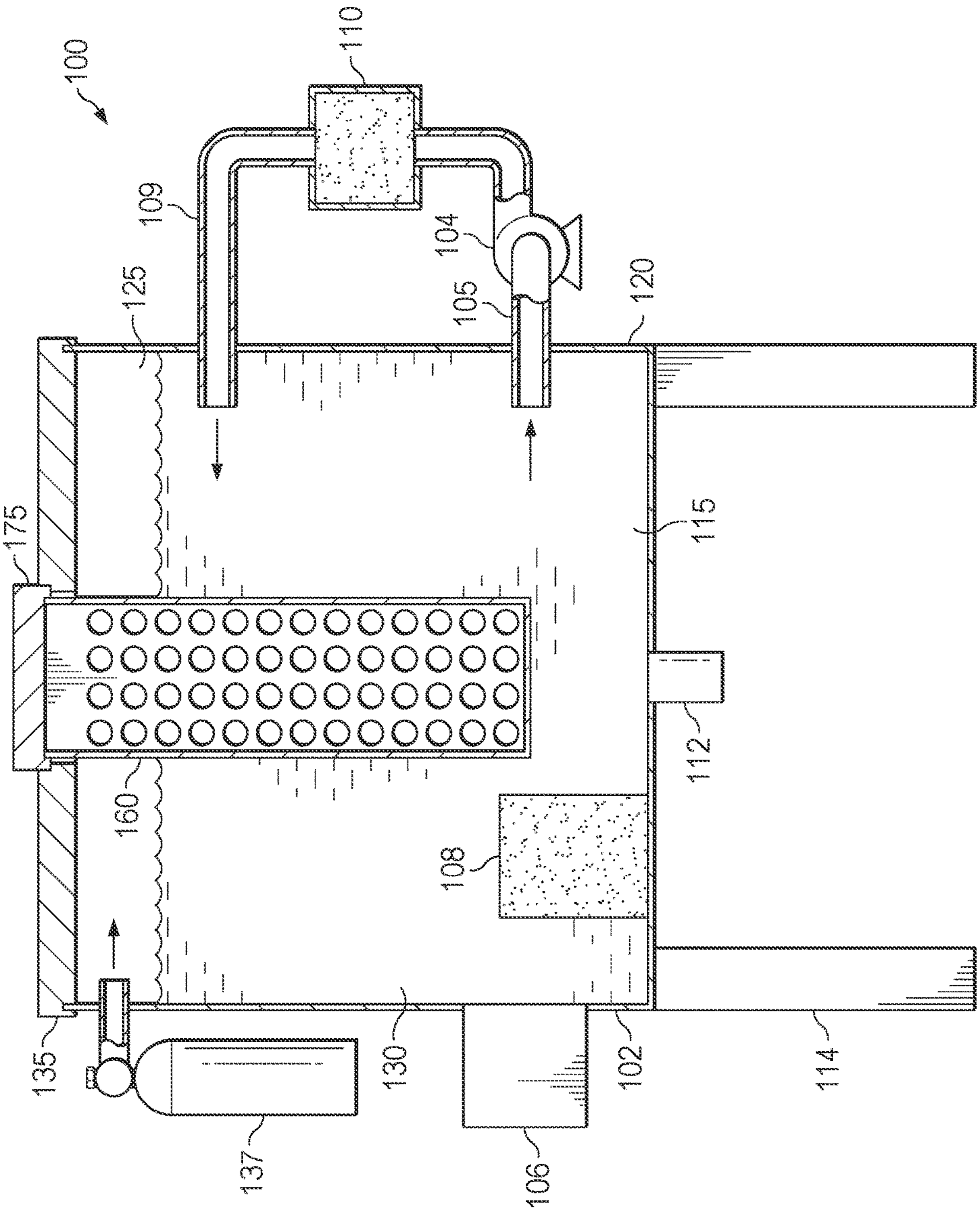
FIG. 1C is an illustration of a perspective view of an alternative beverage flavoring container including a retaining device affixed to a lid section of the beverage flavoring container in accordance with certain embodiments of the present disclosure.

FIG. 1C is an illustration of a perspective view of an alternative beverage flavoring container 100 including a retaining device 160 affixed to a lid section 135 of the beverage flavoring container 100 in accordance with certain embodiments of the present disclosure. As shown, beverage flavoring container 100 includes a body 102 having an interior volume 125. Body 102 further includes a bottom section 115, a sidewall 120 disposed about a perimeter of the bottom section 115, and a lid section 135 affixed to the sidewall 120. At least one retaining device 160 is attached to lid section 135 (more specifically, to cover portion 175 that includes a similar functionality to cover portion 175 of FIG. 1A) and extends into the interior volume 125 of beverage flavoring container 100. Each of the at least one retaining device 160 is configured to retain at least one flavoring agent (not depicted) for suspension of the at least one flavoring agent in alcoholic beverage 130 when beverage flavoring container 100 is at least partially filled with alcoholic beverage 130.

As shown, multiple means for flavoring alcoholic beverage 130 is shown in conjunction with beverage flavoring container 100. One example of a flavoring means includes one or more flavoring agents positioned within the at least one retaining device 160 within beverage flavoring container 100 (as described previously). Another flavoring means includes an inline flavoring filter 110 indirectly affixed to beverage flavoring container 100 and containing one or more flavoring agents. Inline flavoring filter 110 is affixed to an inlet tubing 105 (including a pump 104 for propelling the alcoholic beverage 130 through the inline flavoring filter 110) and an outlet tubing 109 connecting inline flavoring filter 110 to beverage flavoring container 100. An additional flavoring means includes a solitary filter 108 that comprises one or more configurations of a flavoring agent in the form of at least one of sawdust, at least one type of wood chip, a piece of wood, a piece of wood in a lattice configuration, or a wooden lattice structure (including multiple pieces of wood). An additional flavoring means includes oxygen device 137 that may add oxygen to alcoholic beverage 130 in order to alter the flavor profile of alcoholic beverage 130. In an embodiment, beverage flavoring container 100 includes one or more of the flavoring means disclosed.

Beverage flavoring container 100 further includes a heating/cooling unit 106 positioned on beverage flavoring container 100. Heating/cooling unit 106 may be utilized to adjust the temperature within beverage flavoring container 100 and may comprise any of: an electromantle, an electric heating unit, a furnace, a propane/natural gas tank, a radiator/fan unit, a heat pump, an evaporative air conditioner, a water jacket, a heating/cooling jacket, a heat sink, or a steam device. A valve 112 is affixed to bottom section 115 and is configured to release alcoholic beverage 130 from beverage flavoring container 100 for purposes of disposal or moving alcoholic beverage 130 to a different beverage flavoring container 100. Legs 114 are also affixed to bottom section 115 of beverage flavoring apparatus 100 and are configured to support beverage flavoring container 100.

Figure 1D:
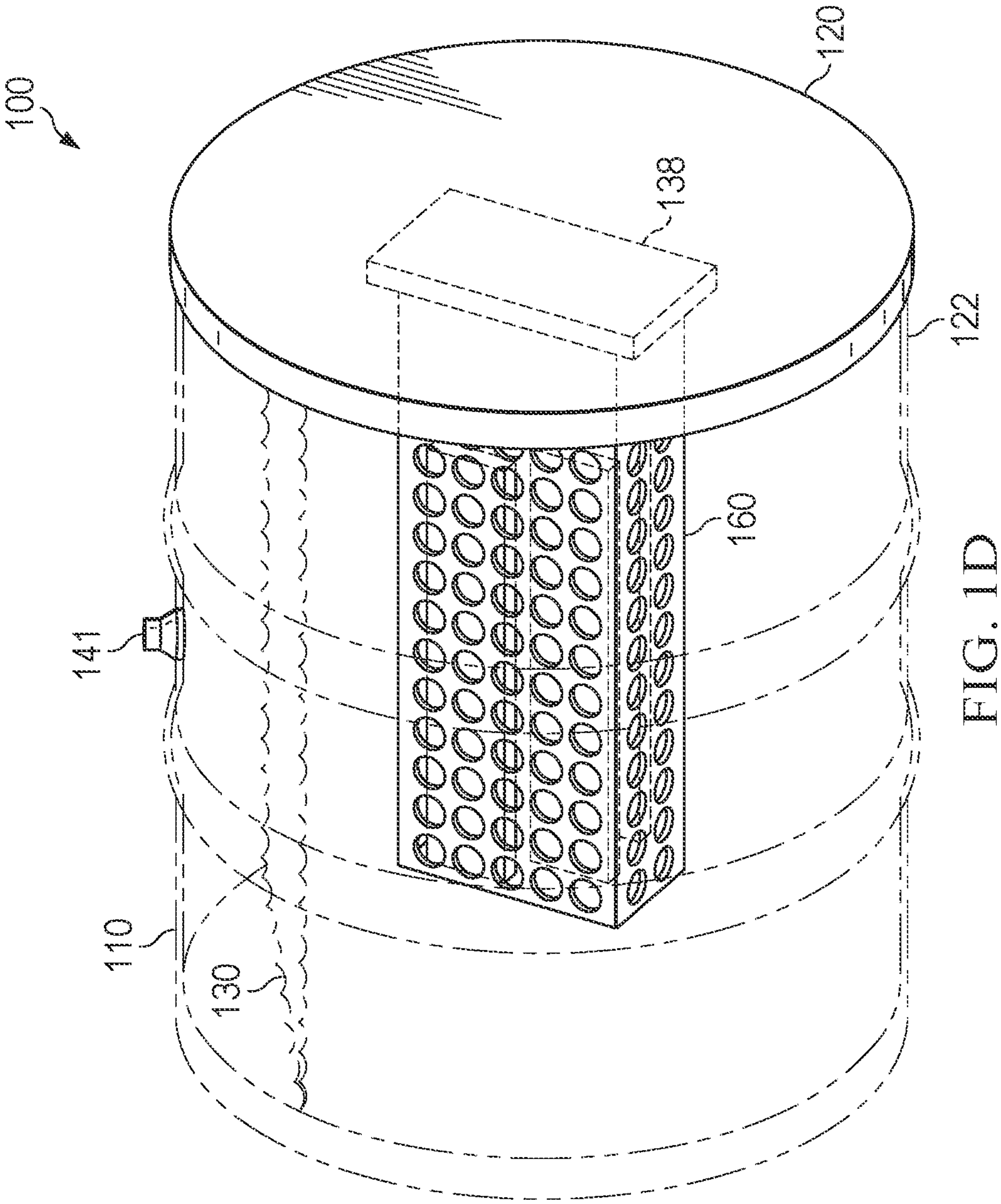
FIG. 1D is an illustration of a perspective view of an alternative beverage flavoring container in accordance with certain embodiments of the present disclosure.

FIG. 1D is an illustration of a perspective view of an alternative beverage flavoring container 100 in accordance with certain embodiments of the present disclosure. As shown, beverage flavoring container 100 is configured as having a greater length than height and includes at least some elements that are similar to elements of other disclosed beverage flavoring containers. Beverage flavoring container 100 includes a body 110 housing an alcoholic beverage 130. A retaining device 160 is affixed to an end 120 and retains at least one flavoring agent within alcoholic beverage 130. A dual inlet/outlet 141 is positioned within a sidewall 122 and is configured for the insertion or extraction of alcoholic beverage 130. In an embodiment, a lid section and/or cover portion 138 (may be similar to any of lid sections/cover portions disclosed) may be positioned adjacent retaining device 160 on end 120 in order to remove at least one of retaining device 160 or flavoring agent(s) from beverage flavoring container 100 when lid section and/or cover portion 138 is/are removed.

Figure 2A:
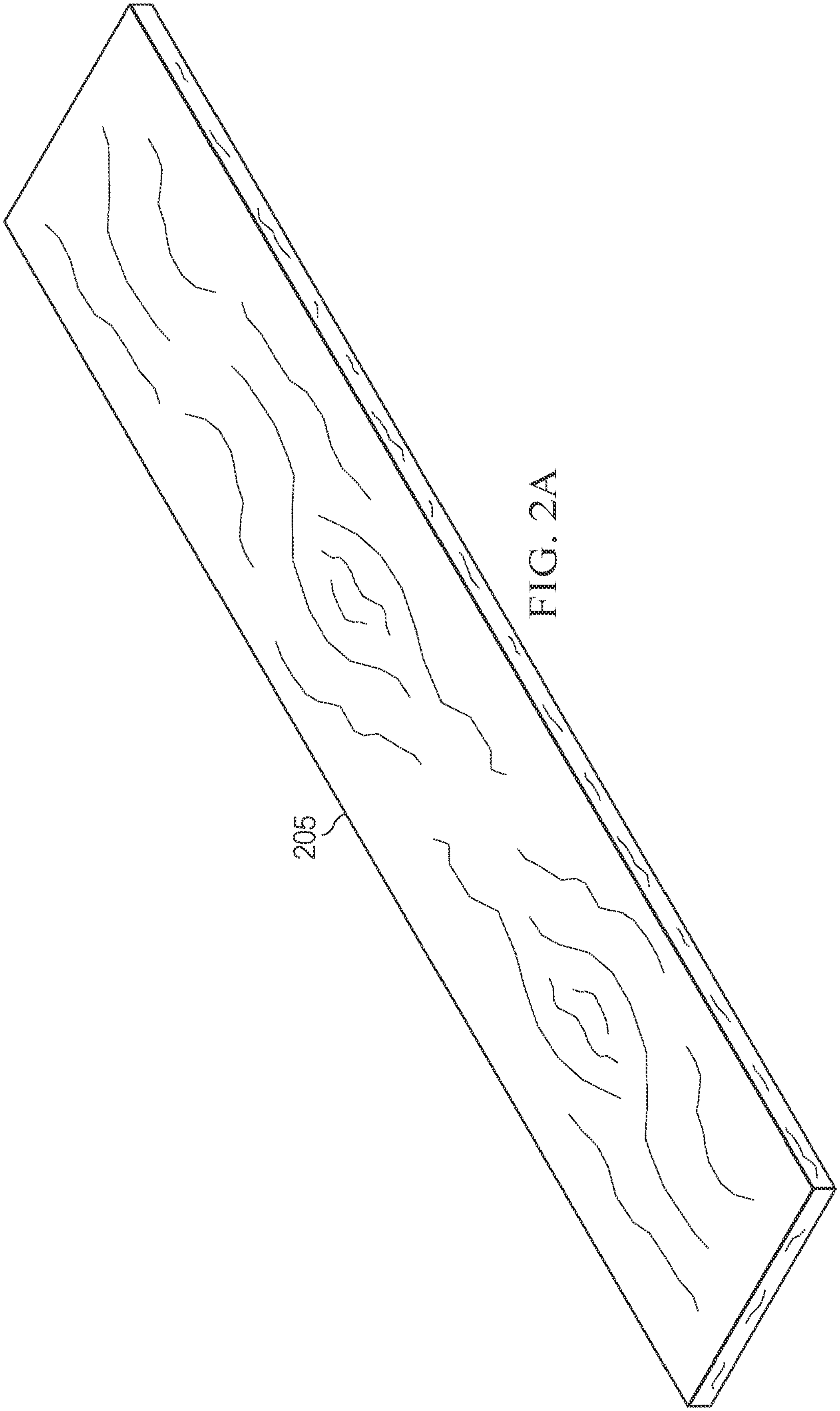
FIG. 2A is an illustration of a perspective view of a flavoring agent in accordance with certain embodiments of the present disclosure.
Figure 2B:
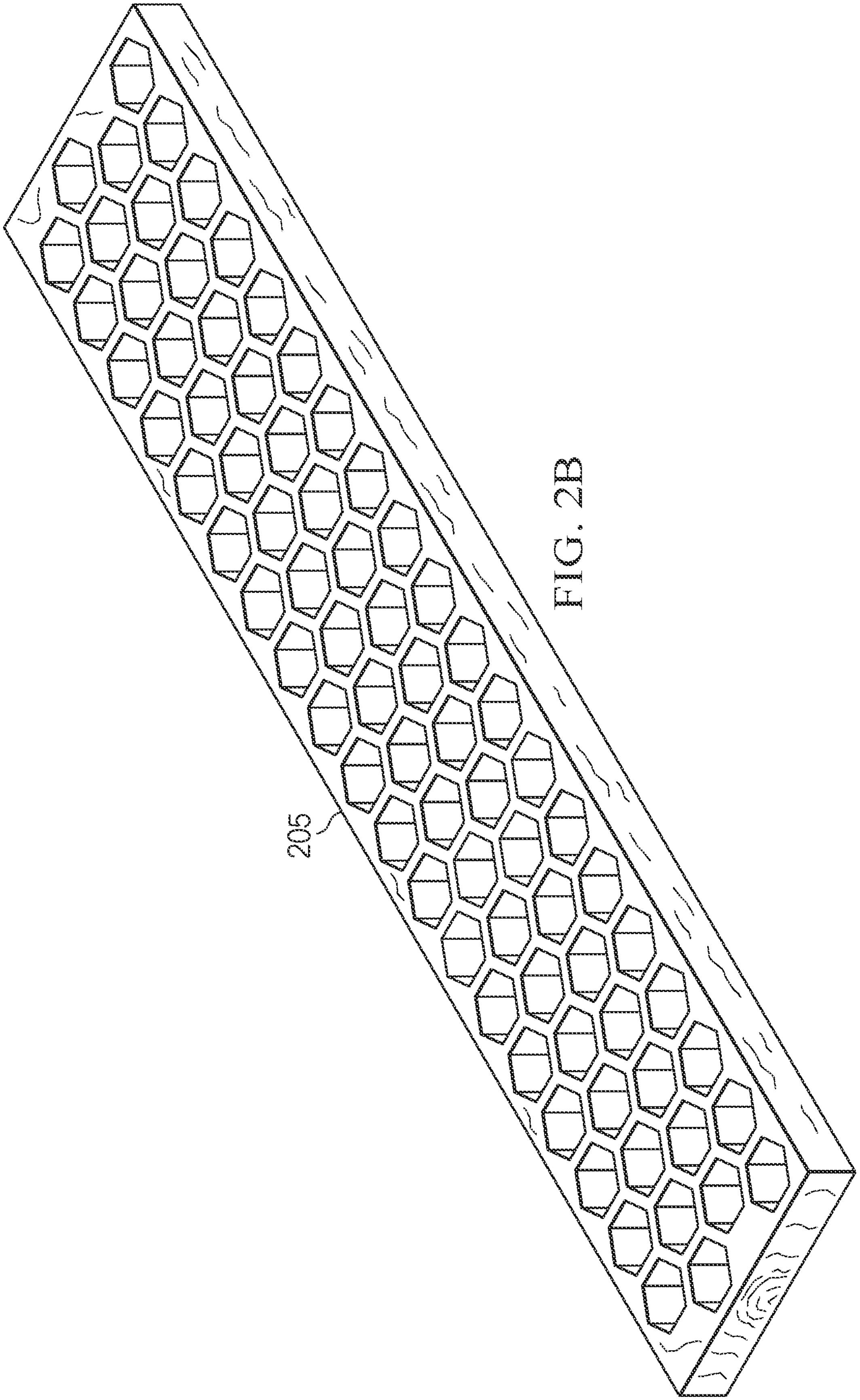
FIG. 2B is an illustration of a perspective view of an alternative flavoring agent embodying a lattice structure in accordance with certain embodiments of the present disclosure.

FIG. 2A is an illustration of a perspective view of a flavoring agent 205 in accordance with certain embodiments of the present disclosure. As shown, flavoring agent 205 is a piece of wood. As further shown in FIG. 2B, an alternative flavoring agent 205 (piece of wood) includes a lattice structure, and more specifically, a honeycomb configuration. The honeycomb configuration is configured to increase surface area exposure of the flavoring agent 205 to an alcoholic beverage. The increased surface area exposure may increase the flavoring agent's 205 ability to flavor an alcoholic beverage and therefore make the flavoring process of an alcoholic beverage shorter. In further embodiments, flavoring agent 205 may comprise any lattice structure configuration that provides increased surface area exposure to an alcoholic beverage.

Figure 2C:
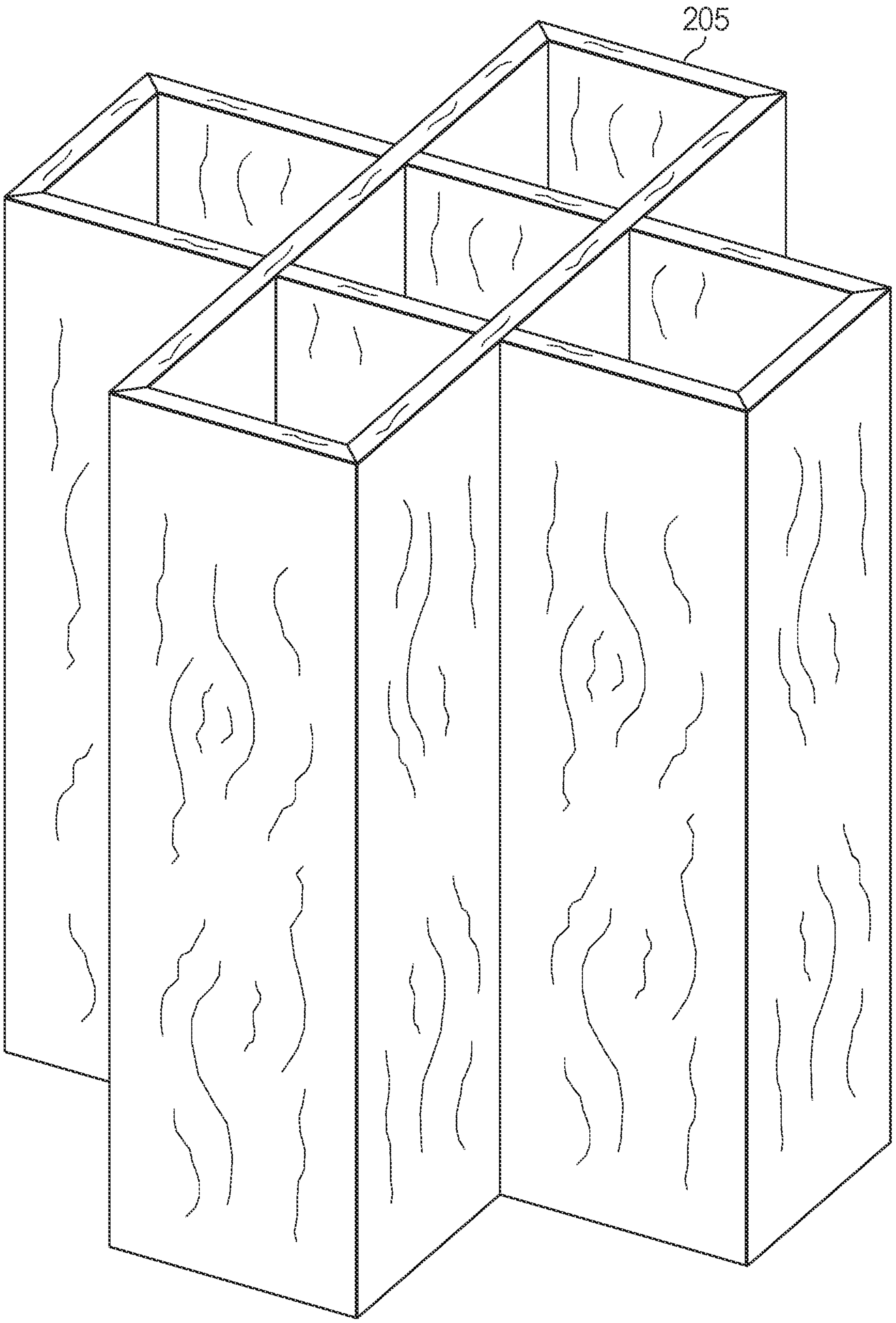
FIG. 2C is an illustration of a perspective view of an alternative flavoring agent in accordance with certain embodiments of the present disclosure.

FIG. 2C is an illustration of a perspective view of an alternative flavoring agent in accordance with certain embodiments of the present disclosure. As shown, flavoring agent 205 is configured as a wood structure (including multiple pieces of wood) having a cross shape or X-shape (lattice configuration) that expands substantially the width and height of the previously disclosed beverage flavoring container(s) in order to provide increased surface area exposure to alcoholic beverages for flavoring purposes (in comparison to the flavoring agents previously presented). In an embodiment, flavoring agent 205 comprises a single type of wood. In an additional embodiment, flavoring agent 205 comprises more than one type of wood in order to provide additional/varied flavor characteristics to an alcoholic beverage. In further embodiments, on a lower end of flavoring agent 205 of FIG. 2C, leg portions may be formed by cutting out a middle portion of wood from each lower end of each piece of wood (for example, a square shape of wood cut out from each lower end of each piece of wood). This leg configuration may provide increased circulation of an alcoholic beverage within one or more interior spaces of the flavoring agent 205 disclosed in FIG. 2C.

Figure 3A:
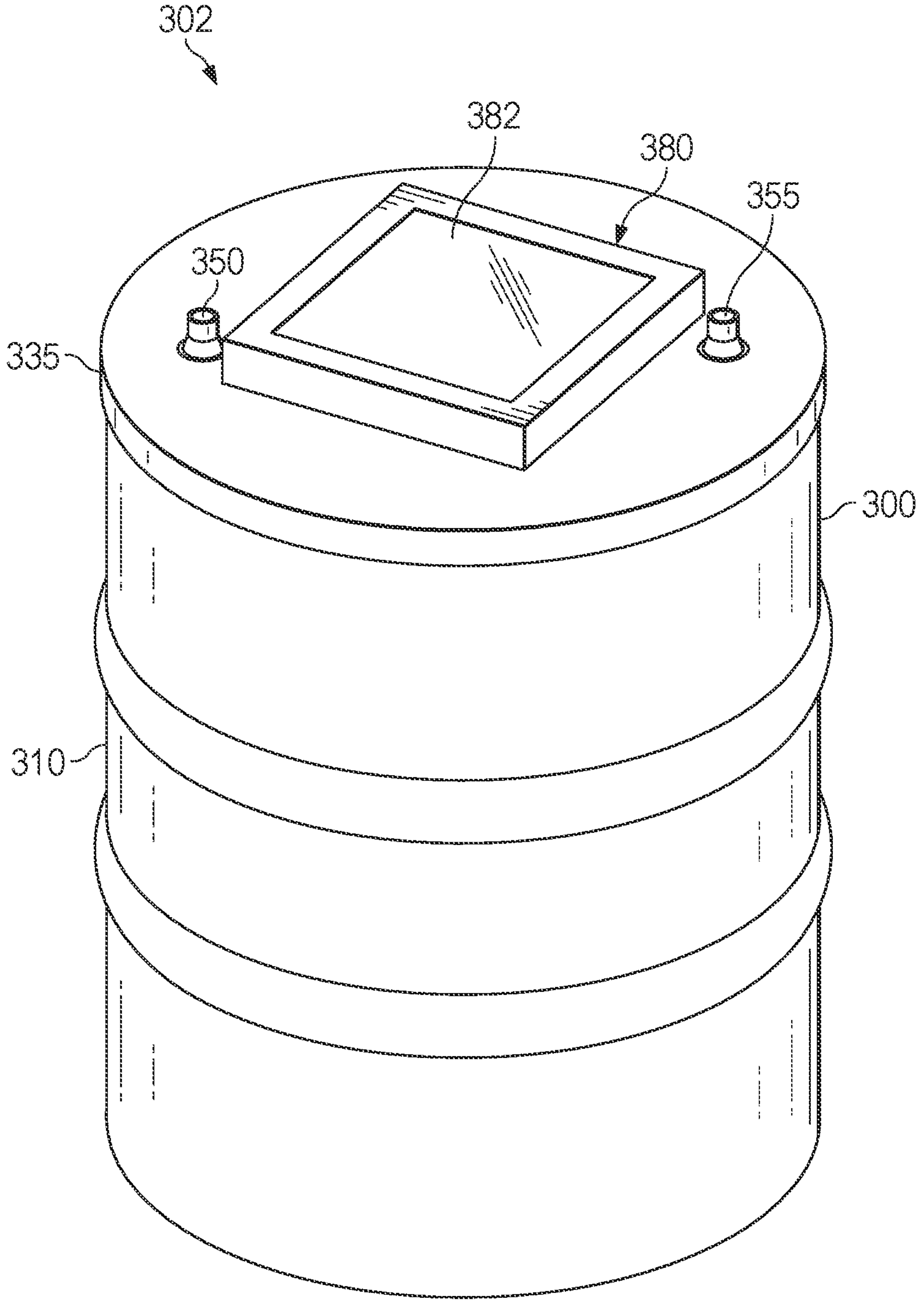
FIG. 3A is an illustration of a perspective view of a beverage flavoring system with a control apparatus integrated into a lid section of a beverage flavoring container in accordance with certain embodiments of the present disclosure.
Figure 3B:
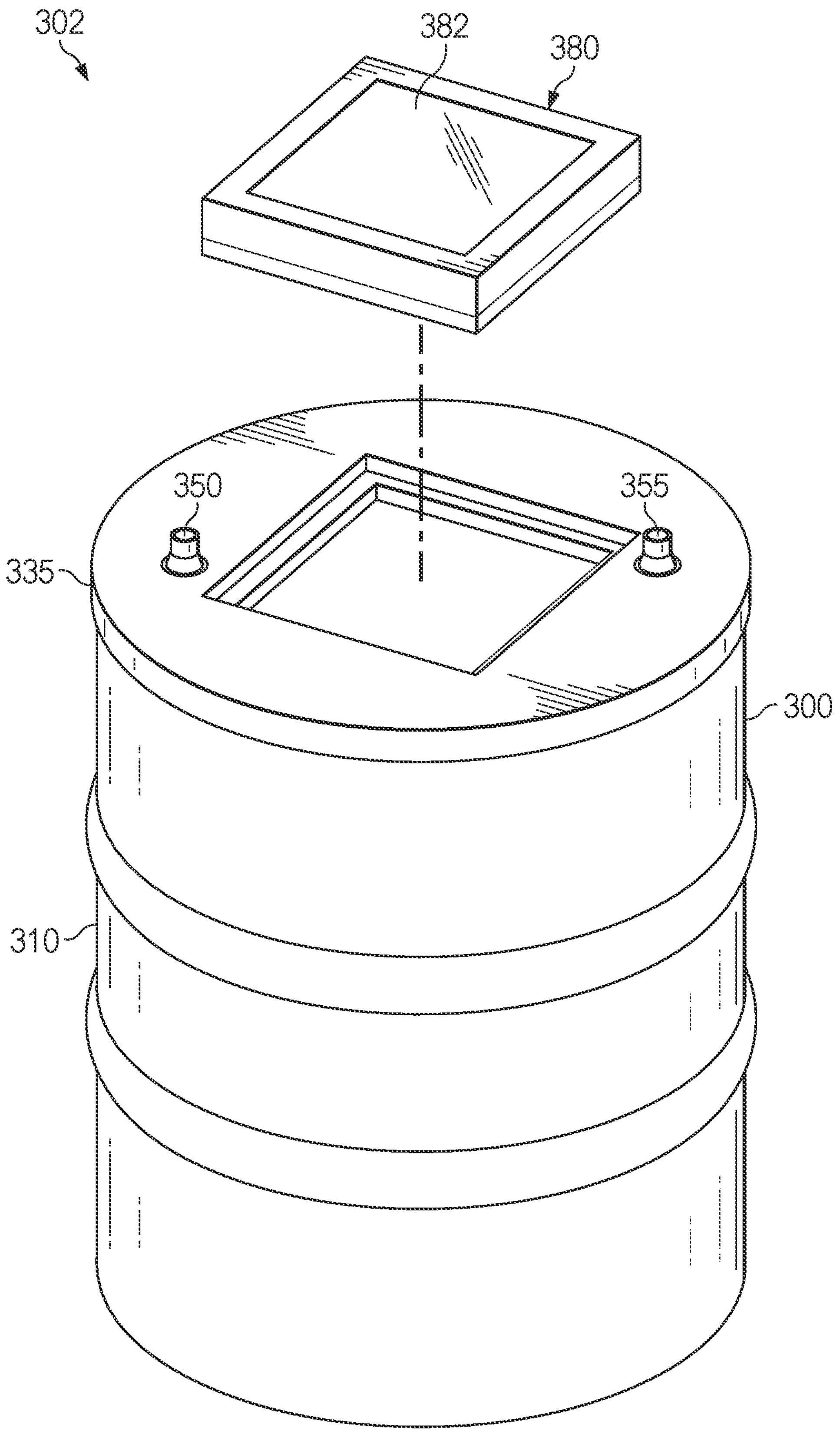
FIG. 3B is an illustration of a perspective view of a beverage flavoring system with a control apparatus removed from a lid section of a beverage flavoring container in accordance with certain embodiments of the present disclosure.

FIG. 3A illustrates a perspective view of a beverage flavoring system 302 with a control apparatus 380 integrated into a lid section 335 of a beverage flavoring container 300 in accordance with certain embodiments of the present disclosure. As shown, beverage flavoring container 300 is similar to beverage flavoring container 100 of FIGS. 1A and 1B. As beverage flavoring system 302, beverage flavoring container 300 includes control apparatus 380 that is integrated into lid section 335 and also includes a user interface 382 configured to receive user input from an individual in relation to a flavoring session. In this embodiment, user interface 382 includes a touchscreen, but in other embodiments, user interface 382 may include one or more tactile push buttons. In other embodiments, as illustrated in FIG. 3B, control apparatus 380 is removably affixed to lid section 335. In further embodiments, control apparatus 380 is removably affixed to either of lid section 335 or body 310 of beverage flavoring container 300.

Figure 3C:
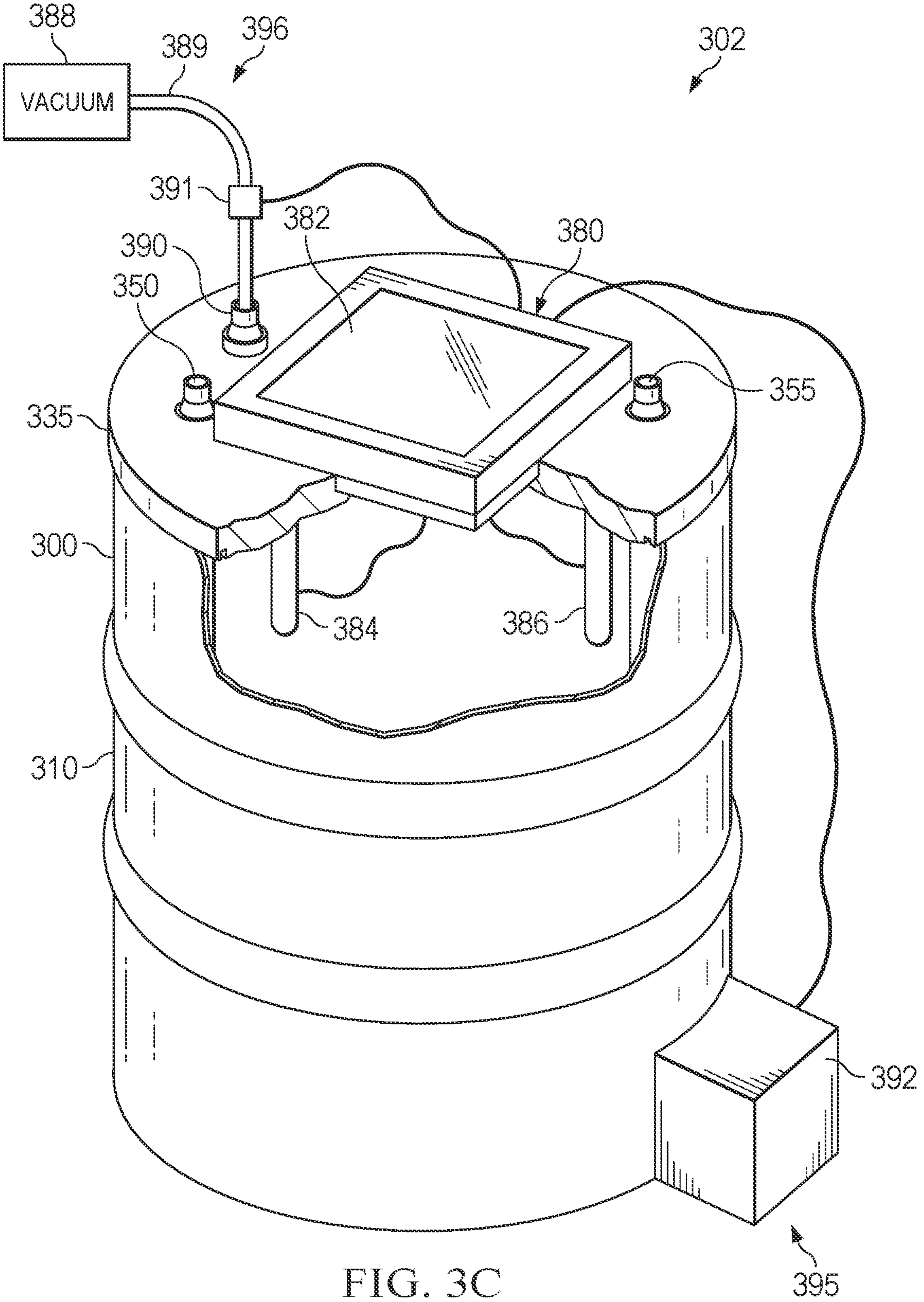
FIG. 3C is an illustration of a partial cutaway view of a beverage flavoring system in accordance with certain embodiments of the present disclosure.

FIG. 3C illustrates a partial cutaway view of a beverage flavoring system 302 in accordance with certain embodiments of the present disclosure. System 302 is configured to regulate an environment of an alcoholic beverage 330. It is noted that FIG. 3C depicts a single beverage flavoring system 302 and, in other embodiments, an alternative system may include more than one of beverage flavoring system 302/beverage flavoring container 300. As shown, system 302 comprises a beverage flavoring container 300 having a body 310 encompassing a sealable chamber for housing the alcoholic beverage 330 and a lid section 335 removably affixable to the body 310. The system 302 further comprises at least one retaining device (not depicted) attached to the lid section 335 and/or at least one flavoring agent without a retaining device (not depicted) and extending into the sealable chamber of the beverage flavoring container 300, where each of the at least one retaining device 360 retains at least one flavoring agent for suspension of the at least one flavoring agent in the alcoholic beverage 330. Pressure and temperature sensors 386,384 are positioned along an interior surface area of the beverage flavoring container 300 and are exposed to the sealable chamber. The pressure and temperature sensors 386,384 are each configured to monitor pressure and temperature of the beverage flavoring container 300 as well as determine voltage signals indicative of a respective one of a pressure or a temperature. Both sensors 384,386 are shown integral with a bottom of lid section 335 while, in other embodiments, can be embedded in a body 310 of the beverage flavoring container 300. It is noted that sensors 384,386 are in wired communication with a control apparatus 380 in order to transmit voltage signals; alternatively, the transmission of voltage signals may be carried out wirelessly. In additional embodiments, beverage flavoring container 300 includes more than one of either of pressure sensor 386 or temperature sensor 384.

A control apparatus 380 in communication with the pressure sensor 386 and the temperature sensor 384 is operable to receive the pressure voltage signal and the temperature voltage signal, receive a setpoint signal indicative of at least one of a desired pressure setpoint or a desired temperature setpoint (via, for example, user input into user interface 382), and control at least one of a pressure regulation signal or a temperature regulation signal such that each of the received pressure voltage signal and the received temperature voltage signal match a respective one of the received setpoint signal. In an embodiment, control apparatus 380 is further operable to receive a setpoint signal indicative of one desired pressure setpoint and one desired temperature setpoint. It is noted that the regulation/adjustment of pressure and temperature in an environment (beverage flavoring container) of an alcoholic beverage leads to an extraction of specific types and quantities of flavoring molecules from flavoring agents that interact with the alcoholic beverage (increase in interactions between alcoholic beverage and flavoring agents) to create a specific flavor for the alcoholic beverage. For example, multiple alcoholic beverages that are each exposed to different pressures and temperatures can create multiple whiskeys with varying flavor profiles.

It is noted that control apparatus 380 is in electrical communication with at least one of a temperature regulation system 395 or a pressure regulation system 396, where each of the at least one temperature regulation system 395 or the pressure regulation system 396 are configured to convert a respective one of the at least one pressure regulation signal or the temperature regulation signal to a respective one of the at least one desired pressure setpoint or the desired temperature setpoint. In an embodiment, the temperature regulation system 395 comprises at least one heating element and/or at least one cooling element integral with the body 310 of the beverage flavoring container 300 in order to adjust the internal temperature of the beverage flavoring container 300. In additional embodiments, the at least one heating element and/or the at least one cooling element comprise any of: an electromantle, an electric heating unit, a furnace, a propane/natural gas tank, a radiator/fan unit, a heat pump, an evaporative air conditioner, a water jacket, a heating/cooling jacket, a heat sink, or a steam device.

In the embodiment shown, pressure regulation system 396 includes a vacuum source 388 that is connected to conduit 389, which introduces to or removes gas from the interior volume of the beverage flavoring container 300 via a gas inlet 390 positioned on lid section 335. A pressure regulator 391 is integrated with conduit 389 and is in wired communication with control apparatus 380. Based on a differential between a pressure voltage signal (from pressure sensor 386) and a pressure setpoint signal (from, for example, user input supplied to user interface 382), control apparatus 380 controls and sends a pressure regulation signal to pressure regulator 391 to adjust the flow of gas flowing into/from beverage flavoring container 300, leading to a change in pressure within beverage flavoring container 300. Additionally in the embodiment shown, temperature regulation system 395 includes a heat/cooling source 392 is affixed to beverage flavoring container 300 and is in wired communication with control apparatus 380. Based on a differential between a temperature voltage signal (from temperature sensor 384) and a temperature setpoint signal (from user input supplied to user interface 382), control apparatus 380 controls and sends a temperature regulation signal to heat/cooling source 392 to adjust the temperature provided to beverage flavoring container 300. In additional embodiments, heat/cooling source 392 may comprise any of: an electromantle, an electric heating unit, a furnace, a propane/natural gas tank, a radiator/fan unit, a heat pump, an evaporative air conditioner, a water jacket, a heating/cooling jacket, a heat sink, or a steam device.

In an embodiment, beverage flavoring container 300 further includes a spectral sensor (see FIG. 6) positioned along an interior surface area of the beverage flavoring container 300, where the spectral sensor is exposed to the sealable chamber. The spectral sensor is configured to collect optical properties of the at least one flavoring agent and/or the alcoholic beverage 330 to determine a presence and concentration of one or more molecules within beverage flavoring container 300. The molecules may originate from the at least one flavoring agent and are configured to provide flavor to the alcoholic beverage 330. In any of the disclosed embodiments, the molecules in a flavoring agent may comprise one or more of: lactones, aldehydes, esters, phenolic compounds (such as, for example, polyphenols and/or volatile phenols), tannins, terpenes, lignins, cellulose, hemicellulose, acids, and/or sugars.

Figure 4A:
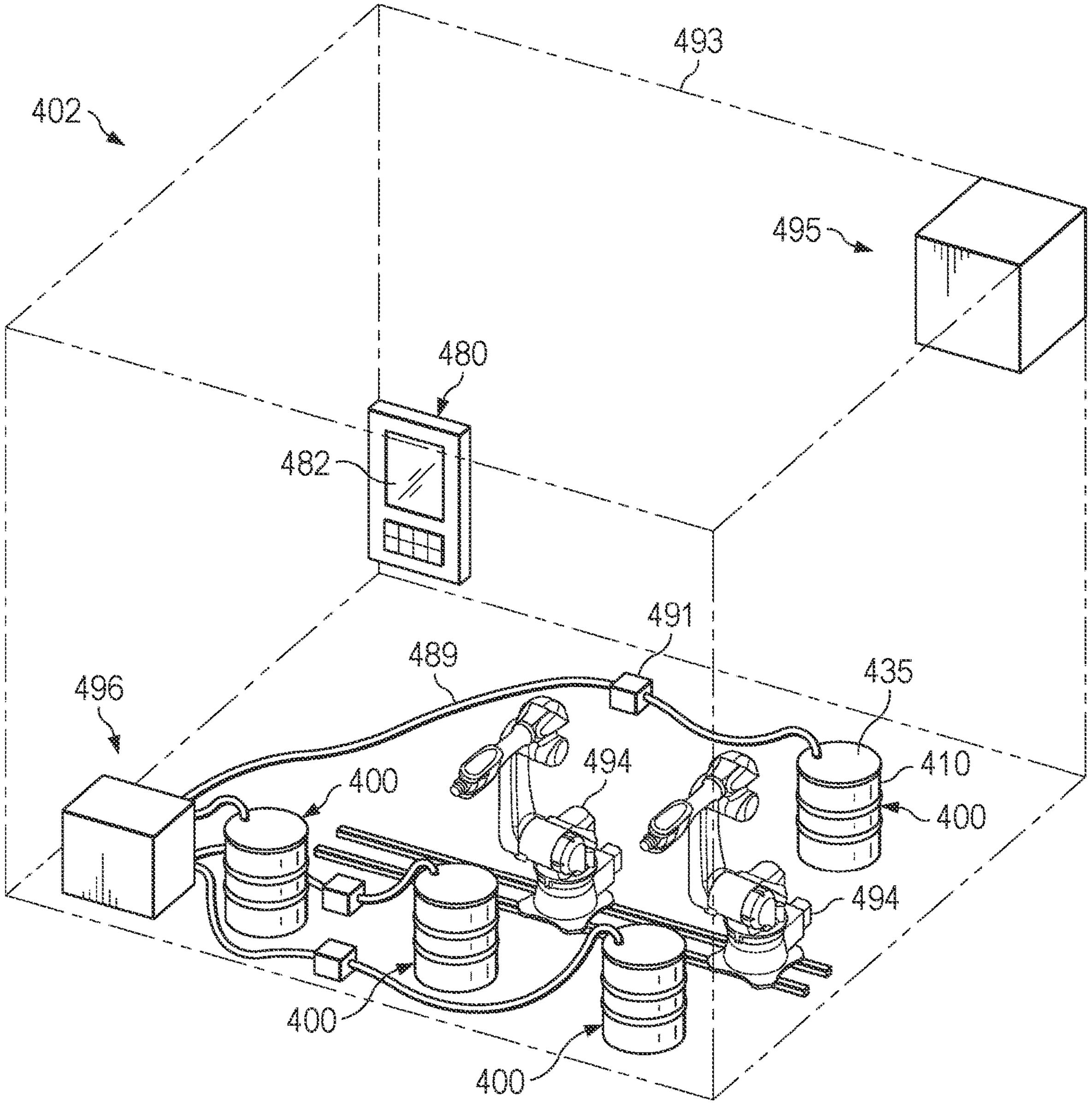
FIG. 4A is an illustration of a perspective view of a beverage flavoring system including multiple beverage flavoring containers in accordance with certain embodiments of the present disclosure.

FIG. 4A illustrates a perspective view of a beverage flavoring system 402 including multiple beverage flavoring containers 400 in accordance with certain embodiments of the present disclosure. System 402 includes a facility 493 (as shown, and alternatively referred to as, enclosed space 493) and at least one beverage flavoring container 400 stored in the enclosed space 493. Each beverage flavoring container 400 includes some or all of the elements disclosed in relation to the elements/embodiments of a beverage flavoring container as found in FIGS. 1A-1C, 2A-2C, and 3A-3C. As shown in this embodiment, a control apparatus 480 is affixed to a wall of enclosed space 493 and includes a user interface 482 for receiving user input. Additionally, a plurality of autonomous robots 494 are positioned adjacent the beverage flavoring containers 400, where control apparatus 480 is operable to instruct one or more of the autonomous robots 494 to interact with one or more of the beverage flavoring containers 400. As further shown, control apparatus 480 is in electrical communication with temperature regulation system 495 and pressure regulation system 496. Control apparatus 480 is configured to receive voltage signals from one or more temperature and/or pressure sensors (not depicted, described previously) of one or more beverage flavoring containers 400. Control apparatus 480 is further configured send instructions to pressure regulation system 496 in order to adjust the pressure of one or more of the beverage flavoring containers 400 shown (connected via conduits). Control apparatus 480 is also configured to send instructions to temperature regulation system 495 in order to adjust the temperature of the one or more beverage flavoring containers 400 shown. In this embodiment, temperature regulation system 495 is configured to adjust the temperature of enclosed space 493 as a whole and not just on a per-container 400 basis. This embodiment of temperature regulation system 495 may be useful where all of the beverage flavoring containers 400 are flavoring the same alcoholic beverage. In an embodiment, control apparatus 480 interacts with the one or more autonomous robots 494, the temperature regulation system 495, and/or the pressure regulation system 496 via at least one of: wired communication or wireless communication.

Figure 4B:
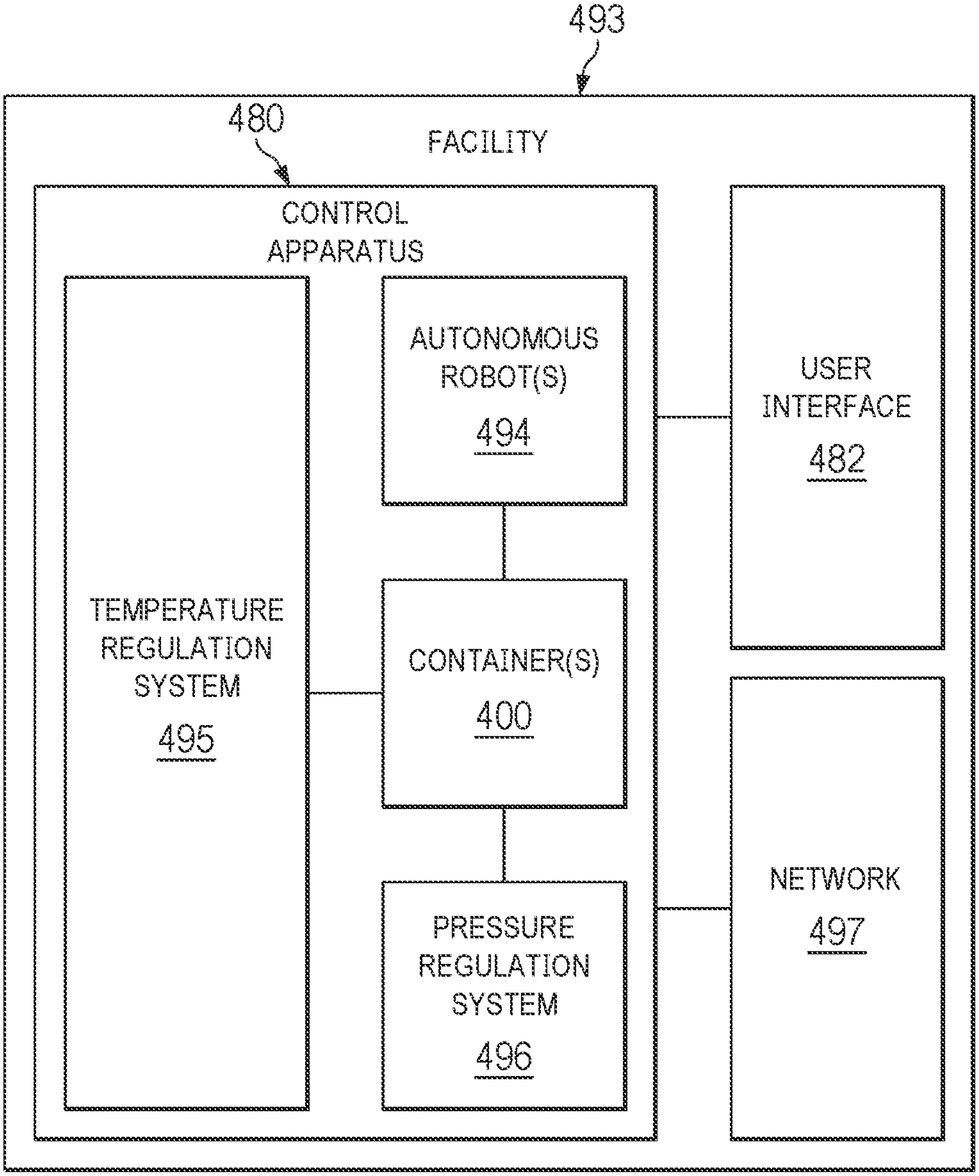
FIG. 4B is an illustration of a diagrammatic view of a beverage flavoring system including multiple beverage flavoring containers in accordance with certain embodiments of the present disclosure.

FIG. 4B illustrates a diagrammatic view of a beverage flavoring system 402 including multiple beverage flavoring containers 400 in accordance with certain embodiments of the present disclosure. System 402 is configured to regulate an environment of at least one alcoholic beverage (not depicted). System 402 comprises an enclosed space 493 and at least one beverage flavoring container 400 stored in the enclosed space 493. Control apparatus 480 is in electrical communication with temperature regulation system 495, pressure regulation system 496, one or more autonomous robots 494, and one or more temperature and one or more pressure sensors in each beverage flavoring container 400 found within enclosed space 493. The control apparatus 480 is operable to: receive the pressure voltage signal and the temperature voltage signal from the pressure sensor 486 and the temperature sensor 484 for each of the at least one beverage flavoring container 400, receive a setpoint signal indicative of at least one of a desired pressure setpoint or a desired temperature setpoint for each of the at least one beverage flavoring container 400, and control at least one of a pressure regulation signal or a temperature regulation signal for each of the at least one beverage flavoring container 400 such that each of the at least one received pressure voltage signal and each of the at least one received temperature voltage signal match a respective one of the at least one received setpoint signal. In embodiments, control apparatus 480 is further operable to receive a setpoint signal indicative of one desired pressure setpoint and one desired temperature setpoint.

It is noted that control apparatus 480 is in electrical communication with at least one of a temperature regulation system 495 or a pressure regulation system 496, where each of the at least one temperature regulation system 495 or the pressure regulation system 496 are configured to convert a respective one of the at least one pressure regulation signal or the temperature regulation signal to at least one environmental output. In an embodiment, a respective one of the at least one environmental output comprises a change in temperature to an entirety of the enclosed space 493. A user interface 482 integral with control apparatus 480 provides user input to control apparatus 480 and may include instructions to adjust the temperature and/or pressure relative of an environment of one or more alcoholic beverages via at least one of temperature regulation system 495 or pressure regulation system 496. Control apparatus 480 is also connected to a network 497 that may provide wireless communication between control apparatus 480 and any of the one or more autonomous robots 494, the temperature regulation system 495, the pressure regulation system 496, and/or any components outside of enclosed space 493.

In embodiments, control apparatus 480 is further operable to instruct one or more autonomous robots 494 to interact with one or more of the at least one beverage flavoring container 400. In additional embodiments, programmable instructions sent from the control apparatus 480 and executable by a processor of each of the at least one autonomous robot 494 cause a gripping device of each of the at least one autonomous robot 494 to perform at least one of: picking up a respective one of the plurality of beverage flavoring containers 400, attaching a hose line (such as, for example conduit 389) to a respective one of the inlet orifice 140 and the outlet orifice 145 (see FIG. 1) of a respective one of the plurality of beverage flavoring containers 400, detaching the hose line to a respective one of the inlet orifice 140 and the outlet orifice 145 of a respective one of the plurality of beverage flavoring containers 400, or replacing one or more of the at least one flavoring agent in a respective one of the at least one retaining device 460.

In an embodiment, each of the at least one flavoring agent comprises a piece of wood. In additional embodiments, each of the at least one piece of wood comprises a honeycomb configuration, where the honeycomb configuration is configured to increase surface area exposure of each of the at least one piece of wood to the alcoholic beverage 430. In additional embodiments, each of the at least one flavoring agent comprises a wood structure having a lattice configuration, where the lattice configuration is configured to increase surface area exposure of each of the at least one flavoring agent to the at least one alcoholic beverage 430.

In an embodiment, each of the at least one beverage flavoring container 400 further includes a spectral sensor (see FIG. 6) positioned along an interior surface area of each of the beverage flavoring containers 400, where the spectral sensor is exposed to the sealable chamber. The spectral sensor is configured to collect optical properties of at least one of the at least one flavoring agent or the alcoholic beverage (not depicted) to determine a presence and concentration of one or more molecules. The molecules may originate from the at least one flavoring agent and are configured to provide flavor to the alcoholic beverage. In any of the disclosed embodiments, the molecules in a flavoring agent may comprise one or more of: lactones, aldehydes, esters, phenolic compounds (such as, for example, polyphenols and/or volatile phenols), tannins, terpenes, lignins, cellulose, hemicellulose, acids, and/or sugars.

Figure 5:
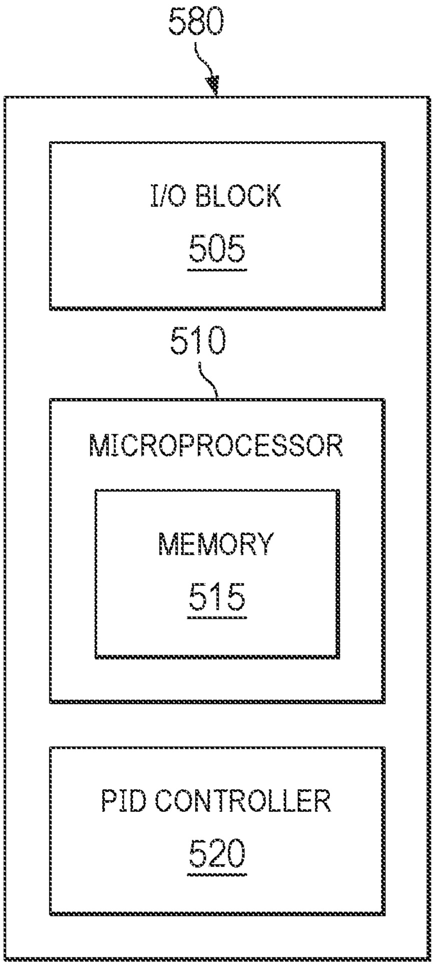
FIG. 5 is an illustration of a schematic of a control apparatus in accordance with certain embodiments of the present disclosure.

FIG. 5 illustrates a schematic of a control apparatus 580 in accordance with certain embodiments of the present disclosure. It is noted that control apparatus 580 can be alternately referred to and generally understood as a "controller", as understood in the art. As shown, control apparatus 580 includes an I/O block 505 that accepts signals from sensors, such as temperature sensor 384 and pressure sensor 386 of FIG. 3. If beverage flavoring system 302 (FIG. 3) is in communication with an external thermostat or other controller, I/O block 505 can provide status and/or other information, and/or accommodate externally-derived control signals, as desired. In certain instances, I/O block 505 may provide appropriate output command signals to pressure regulator 391, or other electrically controlled valve.

Control apparatus 580 additionally includes a microprocessor 510 that may be configured to accept appropriate signals from I/O block 505, and to determine appropriate output signals that can be output via I/O block 505, such as to pressure regulator 391 or heat source 392. Microprocessor 510 may be programmed to accept a temperature voltage signal from one or more temperature sensors, such as temperature sensor 384 (FIG. 3), and to calculate or otherwise determine a command temperature to alter the temperature value received from the temperature sensor 384 in order to account or compensate for temperature differentials and/or thermal lag caused by the partial thermal isolation (if present) of temperature sensor 384 from the alcoholic beverage 330 in beverage flavoring container 300. While not explicitly illustrated, microprocessor 510 may also include memory 515 and/or other components.

It is contemplated that control apparatus 580 may include a control algorithm for operating pressure regulator 391 based on a desired pressure setpoint within beverage flavoring container 300. For example, control apparatus 580 may be configured to provide signals to pressure regulator 391 via wired communication to change the volume of gas flow based on feedback received from user interface 382.

Continuing with FIG. 5, the control apparatus 580 further comprises a proportional-integral-derivative (hereafter "PID") controller 520 that may comprise logic, circuitry, memory, and one or more processing elements (processors). Although a PID controller is illustrated in this specific example, it is to be understood that the PID controller is but one of many potential valve controllers as will be readily apparent to one of ordinary skill in the art. For example, in some embodiments, the PID controller 520 may be substituted for a lead-lag controller, a gain-lead-lag controller (e.g., as described in U.S. Pat. No. 6,962,164 incorporated in its entirety by reference herein), or any other controller sufficient for the application. The controller may be implemented as either hardware or firmware. The PID controller 520 is configured to control the position of a valve within the pressure regulator 391 in accordance with a setpoint indicating a desired pressure setpoint.

Figure 6:
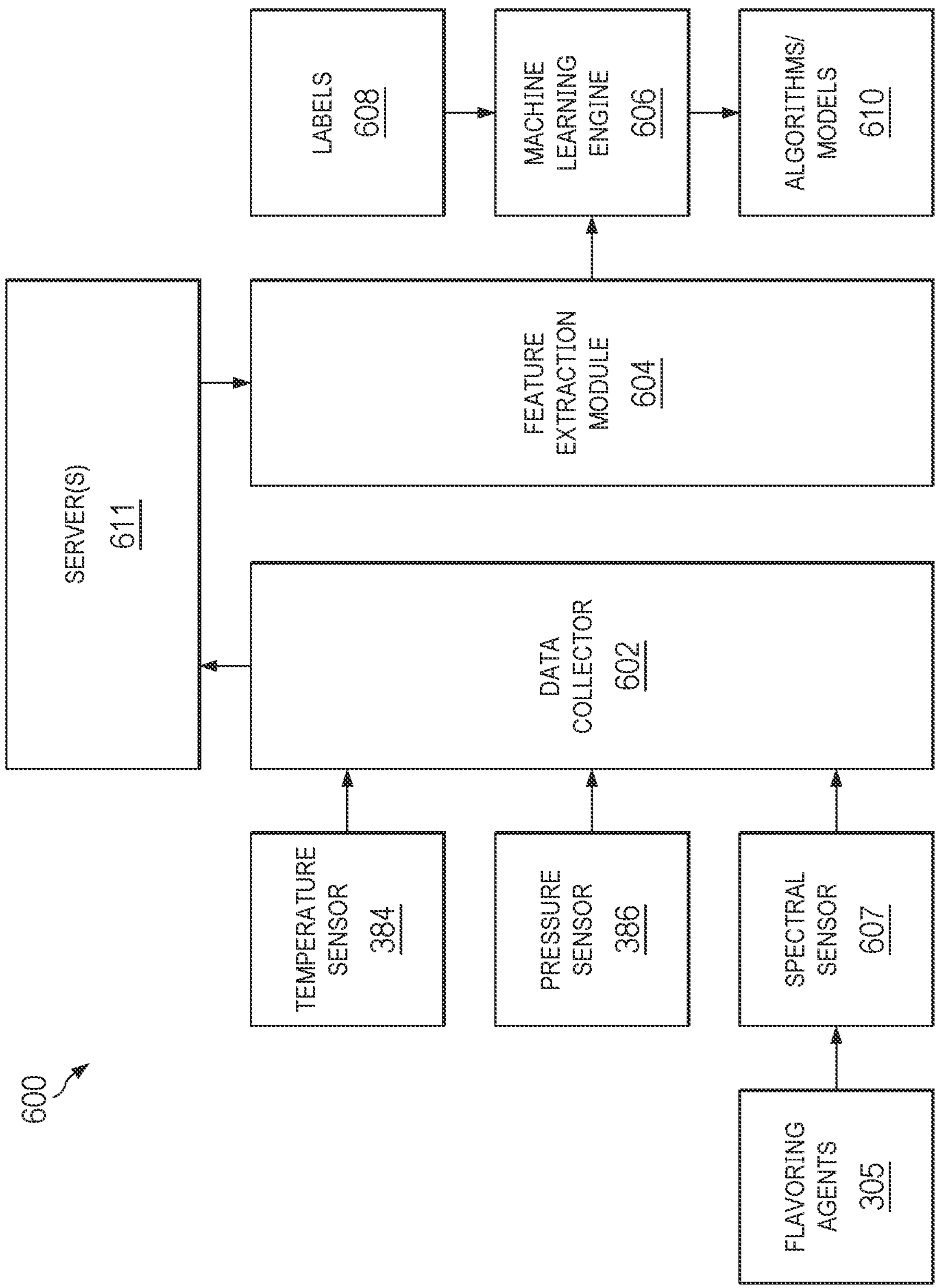
FIG. 6 is an illustration of a block diagram depicting a system for training a machine learning model in accordance with certain embodiments of the present disclosure.

FIG. 6 illustrates a block diagram depicting a system 600 for training a machine learning model in accordance with certain embodiments of the present disclosure. As shown, system 402 includes data collector 602, feature extraction module 604, and machine learning engine 606. In an embodiment, data collector 602 receives environment data from temperature sensor 384 and pressure sensor 386; data collector 602 also receives optical properties of flavoring agents 305 and/or an alcoholic beverage 330 (types and quantities of molecules present) via a spectral sensor 607. Additionally, data collector 602 is configured to store time data relative to the receiving of environmental data and optical properties from temperature sensor 384, pressure sensor 386, and/or spectral sensor 607. The environment data and optical properties are collected during one or more flavoring sessions of at least one alcoholic beverage 330. The environment data and/or optical properties may be locally stored (e.g., on control apparatus 380) or remotely stored on server 611 (as shown in FIG. 6). In certain embodiments, environment data and/or optical properties for a single beverage flavoring container 300 may be stored with an identifier (that, in embodiments, may include time data) on control apparatus 380 (and subsequently, server 611). Upon completion of a flavoring session relative to a single alcoholic beverage 330, data collector 602 may request, for example via user interface 382, that an individual label the single alcoholic beverage 330 (prior to an individual analyzing/tasting an alcoholic beverage 330 or once the individual has analyzed/tasted the alcoholic beverage 330 and has an opinion on the taste/quality/characteristics of the alcoholic beverage 330), and the labels may be stored as labels 608. It is noted that the request for labels may occur for each beverage flavoring container 300 used for a flavoring session.

In an embodiment, feature extraction module 604 may subsequently receive the stored environment data and optical properties, and extract or filter information from the environment data/optical properties based on predetermined criteria. Feature extraction module 604 may then store the extracted or filtered information as extracted features. With respect to extracted features, extracted features may include, for each flavoring session, one or more of: temperature datapoints (environment data), pressure datapoints (environment data), at least one of refractive index data or extinction index data relative to at least one of the at least one flavoring agent or the alcoholic beverage (optical properties), or a timestamp associated with any of the temperature datapoints, the pressure datapoints, or the at least one of the refractive index data or the extinction index data. Timestamp represents a time $T_f$, where $f \geq 0$, recorded at an end of a flavoring session in order to denote a length of time of a flavoring session. Environment data may include data relative to an environment within a beverage flavoring container 300 that is captured at any time, including at time $T_f$, during a flavoring session. For example, environment data may include a temperature or pressure of one or more batches of an alcoholic beverage 330 (e.g., ° F., ° C., psi, atm) captured by temperature sensor 384 or pressure sensor 386. Optical properties may include refractive index and/or extinction index data relative to a flavoring agent 105,205 and/or an alcoholic beverage 330 that is captured at any time, including at time $T_f$, during a flavoring session. For example, optical properties may include measurements of the scattering of light, reflection, absorption, and/or refraction of one or more flavoring agents 105,205 and/or alcoholic beverage 330 captured by spectral sensor 607.

In an embodiment, spectrometer 607 may measure optical properties of (and measure quantities of) molecules originating from a flavoring agent 105,205 (in this case, a flavoring agent made of wood) and that may be present in either of the flavoring agent 105,205 or the alcoholic beverage 330. Molecules may include any of the following: lactones, aldehydes, esters, phenolic compounds (such as, for example, polyphenols and/or volatile phenols), tannins, terpenes, lignins, cellulose, hemicellulose, acids, or sugars. Based on molecular quantity measurements relative to alcoholic beverage 330, either of a char level or a toasting level may be determined for the alcoholic beverage 330 (based on previously presented data correlating molecular quantities with char/toasting levels).

Referring back to FIG. 6, the labels 608 and extracted features are provided to machine learning engine 606. Machine learning engine 606 trains or generates a set of rules, algorithms and/or predictive models 610. In an embodiment, machine learning engine 606 may invoke one or more algorithms/machine learning models (e.g., deep learning frameworks such as recurrent neural networks, deep neural networks, deep belief networks and/or convolutional deep neural networks) to continuously learn flavor characteristics relative each batch/type/flavoring session of alcoholic beverage 330 using the provided labels 608 and extracted features, such that the algorithms/models 610 can be invoked to alter a temperature, a pressure, and or a flavoring agent exposure time of an environment of a beverage flavoring container 300 relative to any batch (or type) of alcoholic beverage 330.

In an embodiment, labels 608 may include any of: alcoholic beverage characteristics or post-flavoring session alcoholic beverage characteristics (which may also include characteristics collected during the flavoring session). Alcoholic beverage characteristics may include, but are not limited to, any of: a char level of one or more flavoring agents, a toasting level of one or more flavoring agents, a mash bill of an alcoholic beverage, a name of an alcoholic beverage, a name of one or more flavoring agents (in the case of a wooden flavoring agent, the name of the type of wood; for example, cedar), a cut of a wood (in the case of a wooden flavoring agent), a surface area of one or more flavoring agents (in the case of a wooden flavoring agent), known molecules in one or more flavoring agents, known temperature or pressure processing parameters, or inert gas exposure type. Post-flavoring session alcoholic beverage characteristics may include, but are not limited to, any of: an aroma, a flavor profile (taste characteristics), a mouth feel, color characteristics, a char level taste characteristic, a toasting level taste characteristic, or a general taste rating based on one or more alcoholic beverage characteristics (such as, for example: good, fair, or poor taste quality).

Figure 7:
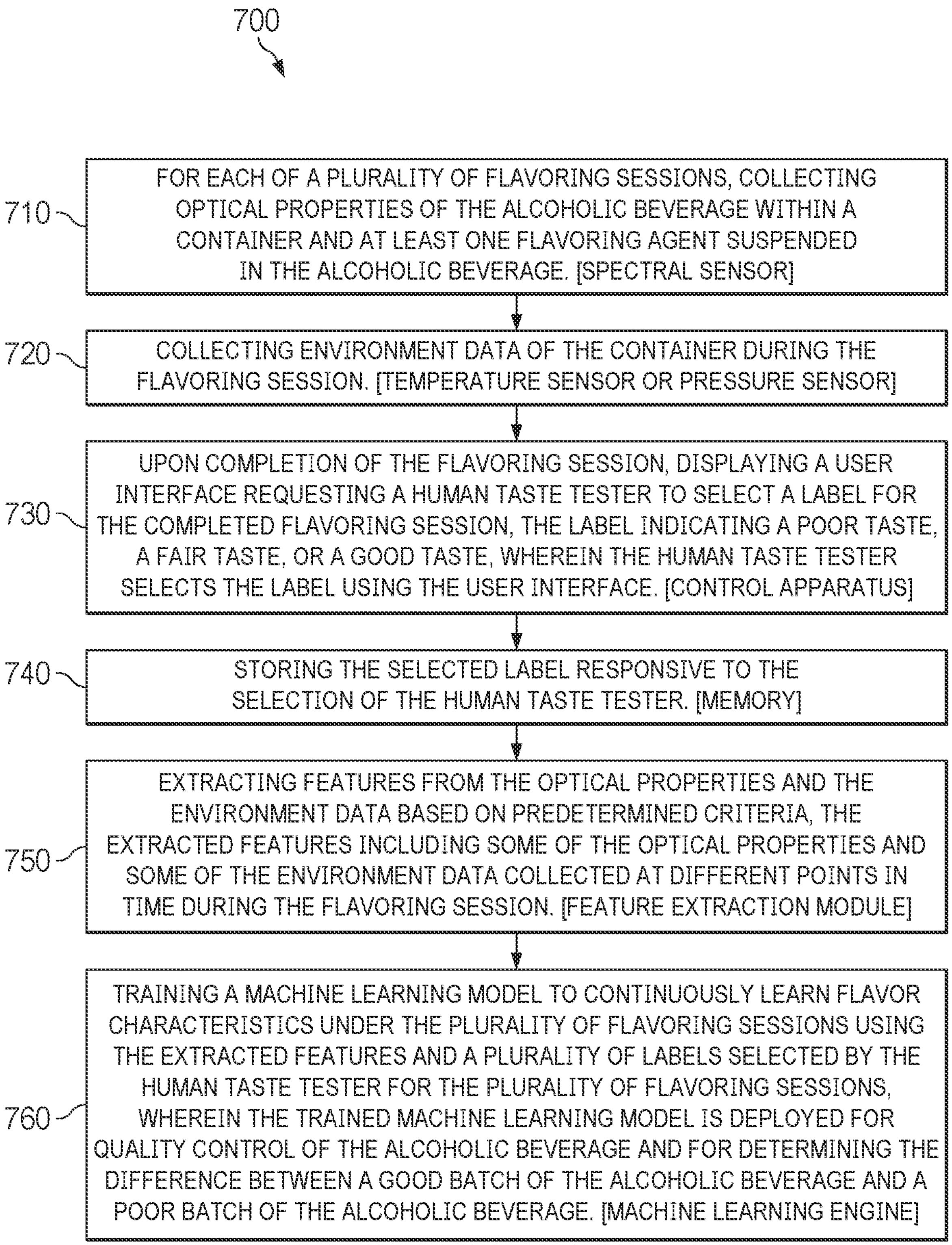
FIG. 7 is an illustration of a flow diagram depicting a method of training a machine learning model for evaluating flavor profiles of an alcoholic beverage in accordance with certain embodiments of the present disclosure.

Reference is now made to FIG. 7, which illustrates a flow diagram depicting a method 700 of training a machine learning model for evaluating flavor profiles of an alcoholic beverage 330 in accordance with certain embodiments of the present disclosure. Flow diagram of method 700 is illustrated as a process in logical flow diagram format, wherein the flow diagram represents a sequence of operations that can be implemented in hardware, software, or a combination thereof. In the context of software, the process represents computer-executable instructions that, when executed by one or more processors, perform the recited operations. Generally, computer-executable instructions may include routines, programs, objects, components, data structures, and the like that perform functions or implement abstract data types. The order in which the operations are described is not intended to be construed as a limitation, and any number of the described processes can be combined in any order and/or performed in parallel to implement the process. For discussion purposes, the method 700 is described with reference to the architecture of an environment 800 (presented subsequently) and systems 300 and 600 of FIGS. 8, 3C, and 6 (respectively).

At block 710, for each of a plurality of flavoring sessions, a spectral sensor 607 collects optical properties of at least one of the alcoholic beverage 330 within a beverage flavoring container 300 or at least one flavoring agent 305 suspended in the alcoholic beverage 330.

At block 720, at least one of a temperature sensor 384 or a pressure sensor 386 collects environment data of the beverage flavoring container 300 during the flavoring session.

At block 730, upon completion of the flavoring session, a control apparatus 380 displays a user interface 382 requesting a human taste tester to select one or more label 608 for the completed flavoring session.

At block 740, a memory 830 (see FIG. 8) stores the selected labels 608 responsive to the selection of the human taste tester.

At block 750, a feature extraction module 604 extracts features from the optical properties and the environment data based on predetermined criteria, where the extracted features include some of the optical properties and some of the environment data collected at different points in time during the flavoring session.

At block 760, a machine learning engine 606 trains a machine learning model 610 to continuously learn flavor characteristics under the plurality of flavoring sessions using the extracted features and the one or more labels 608 selected by the human taste tester for the plurality of flavoring sessions, where the trained machine learning model 610 is deployed for quality control of the alcoholic beverage 330 and for determining the difference between a good batch of the alcoholic beverage 330 and a poor batch of the alcoholic beverage 330.

In an additional embodiment, a system associated with method 700 is presented for training a machine learning model 610 for evaluating flavor profiles of an alcoholic beverage 330. The system comprises a processor 810 and a memory 830 coupled to the processor 810 to store instructions, where the instructions, when executed by the processor 810, cause the processor 810 to perform a number of operations.

One operation includes, for each of a plurality of flavoring sessions, a spectral sensor 607 collecting optical properties of at least one of the alcoholic beverage 330 within a beverage flavoring container 300 or at least one flavoring agent 305 suspended in the alcoholic beverage 330.

Another operation includes at least one of a temperature sensor 384 or a pressure sensor 386 collecting environment data of the beverage flavoring container 300 during the flavoring session.

Another operation includes, upon completion of the flavoring session, a control apparatus 380 displaying a user interface 382 requesting a human taste tester to select one or more label 608 for the completed flavoring session.

Another operation includes a memory 830 (see FIG. 8) storing the selected labels 608 responsive to the selection of the human taste tester.

Another operation includes a feature extraction module 604 extracting features from the optical properties and the environment data based on predetermined criteria, where the extracted features include some of the optical properties and some of the environment data collected at different points in time during the flavoring session.

Another operation includes a machine learning engine 606 training a machine learning model 610 to continuously learn flavor characteristics under the plurality of flavoring sessions using the extracted features and the one or more labels 608 selected by the human taste tester for the plurality of flavoring sessions, where the trained machine learning model 610 is deployed for quality control of the alcoholic beverage 330 and for determining the difference between a good batch of the alcoholic beverage 330 and a poor batch of the alcoholic beverage 330.

In an additional embodiment, a computer program product associated with method 700 is presented for training a machine learning model 610 for evaluating flavor profiles of an alcoholic beverage 330. The computer program product comprises a computer readable storage medium having program instructions embodied therewith, where the program instructions are executable by a processor 810 to cause the processor 810 to perform a number of steps.

One step includes, for each of a plurality of flavoring sessions, a spectral sensor 607 collecting optical properties of at least one of the alcoholic beverage 330 within a beverage flavoring container 300 or at least one flavoring agent 305 suspended in the alcoholic beverage 330.

Another step includes at least one of a temperature sensor 384 or a pressure sensor 386 collecting environment data of the beverage flavoring container 300 during the flavoring session.

Another step includes, upon completion of the flavoring session, a control apparatus 380 displaying a user interface 382 requesting a human taste tester to select one or more label 608 for the completed flavoring session.

Another step includes a memory 830 (see FIG. 8) storing the selected labels 608 responsive to the selection of the human taste tester.

Another step includes a feature extraction module 604 extracting features from the optical properties and the environment data based on predetermined criteria, where the extracted features include some of the optical properties and some of the environment data collected at different points in time during the flavoring session.

Another step includes a machine learning engine 606 training a machine learning model 610 to continuously learn flavor characteristics under the plurality of flavoring sessions using the extracted features and the one or more labels 608 selected by the human taste tester for the plurality of flavoring sessions, where the trained machine learning model 610 is deployed for quality control of the alcoholic beverage 330 and for determining the difference between a good batch of the alcoholic beverage 330 and a poor batch of the alcoholic beverage 330.

In one embodiment, in relation to one or more of method 700, system associated with method 700, and/or computer program product associated with method 700, the collected optical properties of at least one of the alcoholic beverage 330 within the beverage flavoring container 300 or the at least one flavoring agent 305 suspended in the alcoholic beverage 330 determine at least one of: a presence of one or more molecules, a concentration of one or more molecules, or a color of the alcoholic beverage 330.

In a further embodiment, in relation to one or more of method 700, system associated with method 700, and/or computer program product associated with method 700, for each flavoring session, the extracted features include one or more of: temperature datapoints, pressure datapoints, at least one of refractive index data or extinction index data relative to at least one of the at least one flavoring agent 305 or the alcoholic beverage 330, or a timestamp associated with any of the temperature datapoints, the pressure datapoints, or the at least one of the refractive index data or the extinction index data.

In a further embodiment, in relation to one or more of method 700, system associated with method 700, and/or computer program product associated with method 700, the machine learning model 610 is further trained with a database, wherein the database includes information relative to at least one of: alcohol characteristics or wood characteristics.

In a further embodiment, in relation to one or more of method 700, system associated with method 700, and/or computer program product associated with method 700, each of the at least one flavoring agent 305 comprises a wood structure having a lattice configuration, where the lattice configuration configured to increase surface area exposure of each of the at least one flavoring agent 305 to the alcoholic beverage 330.

In a further embodiment, in relation to one or more of method 700, system associated with method 700, and/or computer program product associated with method 700, a label 608 can include any of: a flavor rating of an alcoholic beverage 330 (for example, indicating a poor taste, a fair taste, or a good taste), a char level, a toasting level, an aroma profile, a flavoring profile, a mouth feel rating, a color profile and/or a surface area of a flavoring agent 305. It is noted that a human taste tester can select a label 608 relative to any of the aforementioned data using the user interface 382.

In a further embodiment, in relation to one or more of method 700, system associated with method 700, and/or computer program product associated with method 700, memory 830 may store data relative to one or more flavoring agent 305 and/or one or more alcoholic beverage 330 to use for the training of the machine learning model 610. This data may relate to any of the following in relation to one or more flavoring agents 305 and/or one or more alcoholic beverage 330: mash, fermentation, distillation, or blending.

In a further embodiment, in relation to one or more of method 700, system associated with method 700, and/or computer program product associated with method 700, environment data may additionally include oxygen levels of an environment within a beverage flavoring container 300 and may be measured via an oxygen sensor.

For the purposes of this disclosure, and in relation to one or more of method 700, system associated with method 700, and/or computer program product associated with method 700, in some embodiments, "alcoholic beverage 330" may refer to more than one batch of a single type of alcohol (for example, more than one batch of whiskey, rum, tequila, or gin). In other embodiments, "alcoholic beverage 330" may refer to more than one batch of multiple types of alcohols.

Figure 8:
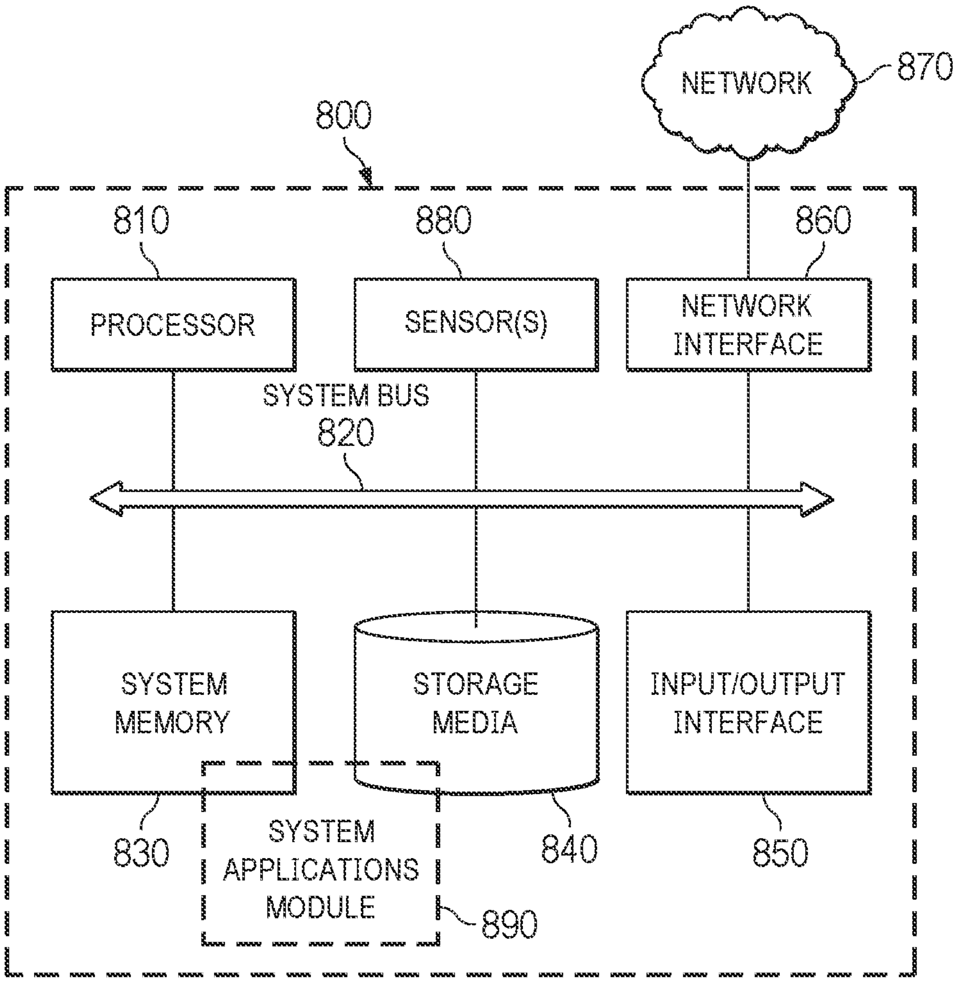
FIG. 8 is an illustration of a computing machine and a system applications module, in accordance with certain example embodiments.

Referring now to FIG. 8, illustrated is a computing machine 800 and a system applications module 890, in accordance with example embodiments. The computing machine 800 can correspond to any of the various computers, mobile devices, laptop computers, Internet of Things (IoT), servers, embedded systems, or computing systems presented herein. The module 890 can comprise one or more hardware or software elements, e.g. other OS application and user and kernel space applications, designed to facilitate the computing machine 800 in performing the various methods and processing functions presented herein. The computing machine 800 can include various internal or attached components such as a processor 810, system bus 820, system memory 830, storage media 840, input/output interface 850, a network interface 860 for communicating with a network 870, e.g. cellular/GPS, Bluetooth, WIFI, or Devicenet, EtherCAT, Analog, RS485, etc., and one or more sensors 880.

The computing machines can be implemented as a conventional computer system, an embedded controller, a laptop, a server, a mobile device, a smartphone, a wearable computer, a customized machine, any other hardware platform, or any combination or multiplicity thereof. The computing machines can be a distributed system configured to function using multiple computing machines interconnected via a data network or bus system.

Processor 810 can be designed to execute code instructions in order to perform the operations and functionality described herein, manage request flow and address mappings, and to perform calculations and generate commands. Processor 810 can be configured to monitor and control the operation of the components in the computing machines. Processor 810 can be a general purpose processor, a processor core, a multiprocessor, a reconfigurable processor, a microcontroller, a digital signal processor ("DSP"), an application specific integrated circuit ("ASIC"), a controller, a state machine, gated logic, discrete hardware components, any other processing unit, or any combination or multiplicity thereof. Processor 810 can be a single processing unit, multiple processing units, a single processing core, multiple processing cores, special purpose processing cores, co-processors, or any combination thereof. According to certain embodiments, processor 810 along with other components of computing machine 800 can be a software based or hardware based virtualized computing machine executing within one or more other computing machines. In another embodiment, for example, such aforementioned components can be implemented as software installed and stored in a persistent storage device, which can be loaded and executed in a memory by processor 810 to carry out the processes or operations described throughout this application. Alternatively, the components can be implemented as executable code programmed or embedded into dedicated hardware such as an integrated circuit (e.g., an application specific IC or ASIC), a digital signal processor (DSP), or a field programmable gate array (FPGA), which can be accessed via a corresponding driver and/or operating system from an application. Furthermore, the components can be implemented as specific hardware logic in a processor or processor core as part of an instruction set accessible by a software component via one or more specific instructions.

The system memory 830 can include non-volatile memories such as read-only memory ("ROM"), programmable read-only memory ("PROM"), erasable programmable read-only memory ("EPROM"), flash memory, or any other device capable of storing program instructions or data with or without applied power. The system memory 830 can also include volatile memories such as random access memory ("RAM"), static random access memory ("SRAM"), dynamic random access memory ("DRAM"), and synchronous dynamic random access memory ("SDRAM"). Other types of RAM also can be used to implement the system memory 830. The system memory 830 can be implemented using a single memory module or multiple memory modules. While the system memory 830 is depicted as being part of the computing machine, one skilled in the art will recognize that the system memory 830 can be separate from the computing machine 800 without departing from the scope of the subject technology. It should also be appreciated that the system memory 830 can include, or operate in conjunction with, a non-volatile storage device such as the storage media 840.

The storage media 840 can include a hard disk, a floppy disk, a compact disc read-only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 840 can store one or more operating systems, application programs and program modules, data, or any other information. The storage media 840 can be part of, or connected to, the computing machine. The storage media 840 can also be part of one or more other computing machines that are in communication with the computing machine such as servers, database servers, cloud storage, network attached storage, and so forth.

The applications module 890 and other OS application modules can comprise one or more hardware or software elements configured to facilitate the computing machine with performing the various methods and processing functions presented herein. The applications module 890 and other OS application modules can include one or more algorithms or sequences of instructions stored as software or firmware in association with the system memory 830, the storage media 840 or both. The storage media 840 can therefore represent examples of machine or computer readable media on which instructions or code can be stored for execution by the processor 810. Machine or computer readable media can generally refer to any medium or media used to provide instructions to the processor 810. Such machine or computer readable media associated with the applications module 890 and other OS application modules can comprise a computer software product. It should be appreciated that a computer software product comprising the applications module 890 and other OS application modules can also be associated with one or more processes or methods for delivering the applications module 890 and other OS application modules to the computing machine via a network, any signal-bearing medium, or any other communication or delivery technology. The applications module 890 and other OS application modules can also comprise hardware circuits or information for configuring hardware circuits such as microcode or configuration information for an FPGA or other PLD. In one exemplary embodiment, applications module 890 and other OS application modules can include algorithms capable of performing the functional operations described by the flow charts (modes of operation) computer systems presented herein.

The input/output ("I/O") interface 850 can be configured to couple to one or more external devices, to receive data from the one or more external devices, and to send data to the one or more external devices. Such external devices along with the various internal devices can also be known as peripheral devices. The I/O interface 850 can include both electrical and physical connections for coupling the various peripheral devices to the computing machine or the processor 810. The I/O interface 850 can be configured to communicate data, addresses, and control signals between the peripheral devices, the computing machine, or the processor 810. The I/O interface 850 can be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface 850 can be configured to implement only one interface or bus technology. Alternatively, the I/O interface 850 can be configured to implement multiple interfaces or bus technologies. The I/O interface 850 can be configured as part of, all of, or to operate in conjunction with, the system bus 820. The I/O interface 850 can include one or more buffers for buffering transmissions between one or more external devices, internal devices, the computing machine, or the processor 820.

The I/O interface 820 can couple the computing machine to various input devices including mice, touch-screens, scanners, electronic digitizers, sensors, receivers, touchpads, trackballs, cameras, microphones, keyboards, any other pointing devices, or any combinations thereof. The I/O interface 820 can couple the computing machine to various output devices including video displays, speakers, printers, projectors, tactile feedback devices, automation control, robotic components, actuators, motors, fans, solenoids, valves, pumps, transmitters, signal emitters, lights, and so forth.

The computing machine 800 can operate in a networked environment using logical connections through the NIC 860 to one or more other systems or computing machines across a network. The network can include wide area networks (WAN), local area networks (LAN), intranets, the Internet, wireless access networks, wired networks, mobile networks, telephone networks, optical networks, or combinations thereof. The network can be packet switched, circuit switched, of any topology, and can use any communication protocol. Communication links within the network can involve various digital or an analog communication media such as fiber optic cables, free-space optics, waveguides, electrical conductors, wireless links, antennas, radio-frequency communications, and so forth.

The one or more sensors 880 can be a position sensor and pressure sensors. The pressure sensor can be an Absolute Pressure (P) sensor or a Differential Pressure (DP) sensor. The position sensor can be a capacitive, optical, strain gauge, or magnetic sensor. The sensors 880 can be traditional sensors or semiconductor based sensors.

The processor 810 can be connected to the other elements of the computing machine or the various peripherals discussed herein through the system bus 820. It should be appreciated that the system bus 820 can be within the processor 810, outside the processor 810, or both. According to some embodiments, any of the processors 810, the other elements of the computing machine, or the various peripherals discussed herein can be integrated into a single device such as a system on chip ("SOC"), system on package ("SOP"), or ASIC device.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions unless otherwise disclosed for an exemplary embodiment. Further, a skilled programmer would be able to write such a computer program to implement an embodiment of the disclosed embodiments based on the appended flow charts, algorithms and associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described previously. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

Figure 9:
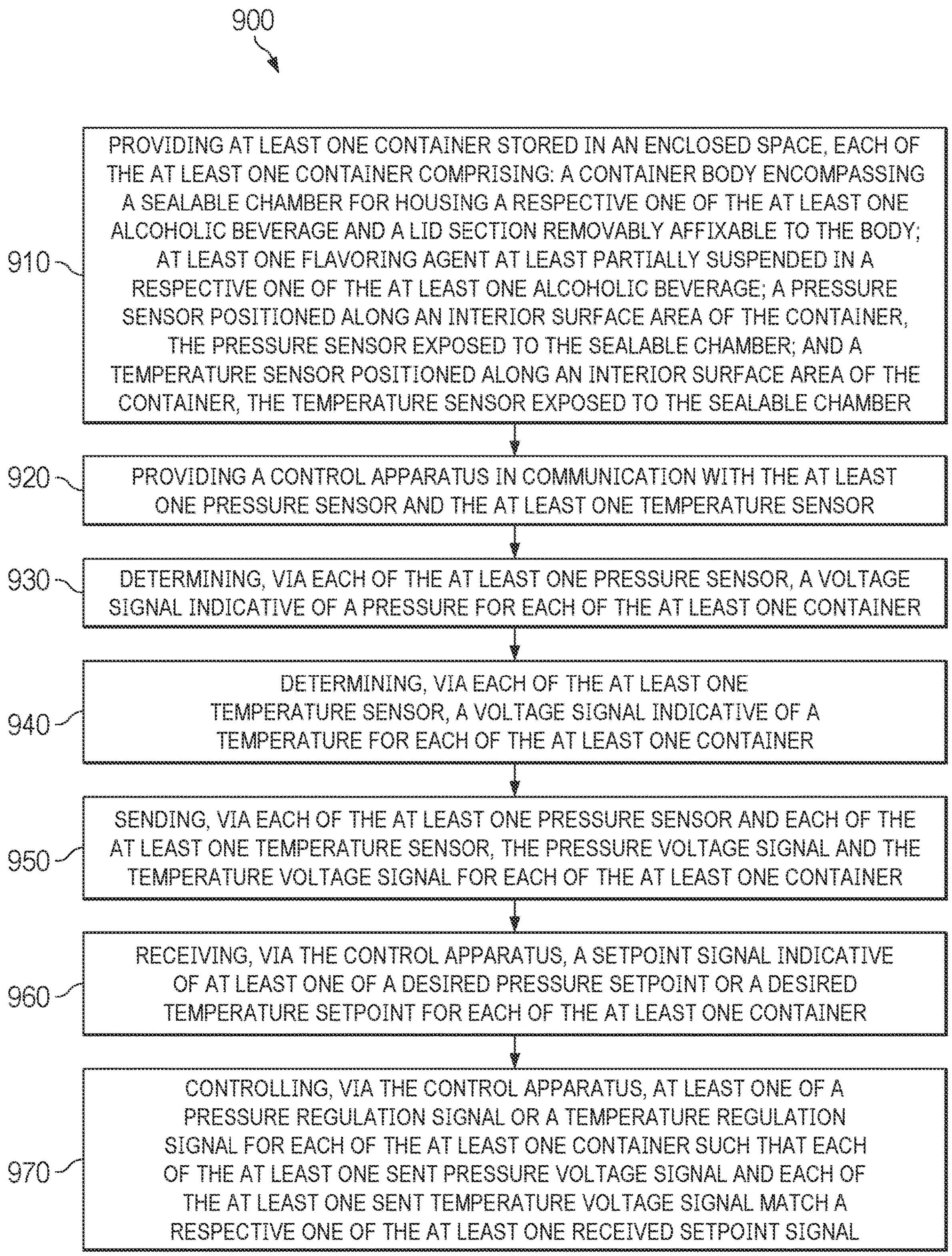
FIG. 9 is an illustration of a flow diagram depicting a method for regulating an environment of at least one alcoholic beverage in accordance with certain embodiments of the present disclosure.

Reference is now made to FIG. 9, which illustrates a flow diagram depicting a method 900 for regulating an environment of at least one alcoholic beverage 430 in accordance with certain embodiments of the present disclosure. Flow diagram of method 900 is illustrated as a process in logical flow diagram format, wherein at least a portion of the flow diagram represents a sequence of operations that can be implemented in hardware, software, or a combination thereof. In the context of software, the process represents computer-executable instructions that, when executed by one or more processors, perform the recited operations. Generally, computer-executable instructions may include routines, programs, objects, components, data structures, and the like that perform functions or implement abstract data types. The order in which the operations are described is not intended to be construed as a limitation, and any number of the described processes can be combined in any order and/or performed in parallel to implement the process. For discussion purposes, the method 900 is described with reference to the architecture of environment 800 and systems 402 and 600 of FIGS. 8, 4B, and 6 (respectively).

At block 910, method 900 includes providing at least one beverage flavoring container 400 stored in an enclosed space 493, where each of the at least one beverage flavoring container 400 includes a beverage flavoring container body 410 encompassing a sealable chamber for housing a respective one of the at least one alcoholic beverage 430. Each of the at least one beverage flavoring container 400 further includes a lid section 435 removably affixable to the body 410 and at least one flavoring agent 305 at least partially suspended in a respective one of the at least one alcoholic beverage 430. Each of the at least one beverage flavoring container 400 further includes a pressure sensor 486 positioned along an interior surface area of the beverage flavoring container 400 and being exposed to the sealable chamber; additionally, a temperature sensor 484 is positioned along an interior surface area of the beverage flavoring container 400 and being exposed to the sealable chamber.

At block 920, method 900 includes providing a control apparatus 480 in communication with the at least one pressure sensor 486 and the at least one temperature sensor 484.

At block 930, method 900 includes determining, via each of the at least one pressure sensor 486, a voltage signal indicative of a pressure for each of the at least one beverage flavoring container 400.

At block 940, method 900 includes determining, via each of the at least one temperature sensor 484, a voltage signal indicative of a temperature for each of the at least one beverage flavoring container 400.

At block 950, method 900 includes sending, via each of the at least one pressure sensor 486 and each of the at least one temperature sensor 484, the pressure voltage signal and the temperature voltage signal for each of the at least one beverage flavoring container 400.

At block 960, method 900 includes receiving, via the control apparatus 480, a setpoint signal indicative of at least one of a desired pressure setpoint or a desired temperature setpoint for each of the at least one beverage flavoring container 400.

At block 970, method 900 includes controlling, via the control apparatus 480, at least one of a pressure regulation signal or a temperature regulation signal for each of the at least one beverage flavoring container 400 such that each of the at least one sent pressure voltage signal and each of the at least one sent temperature voltage signal match a respective one of the at least one received setpoint signal.

In one embodiment, control apparatus 480 is in electrical communication with at least one of a temperature regulation system 495 or a pressure regulation system 496.

In a further embodiment, the integration workflow of the flow diagram of method 900 further includes converting, via each of the at least one temperature regulation system 495 or the pressure regulation system 496, a respective one of the at least one pressure regulation signal or the temperature regulation signal to at least one environmental output.

In a further embodiment, a respective one of the at least one environmental output comprises a change in temperature to an entirety of the enclosed space 493.

In a further embodiment, control apparatus 480 is further operable to receive a setpoint signal indicative of one desired pressure setpoint and one desired temperature setpoint.

In a further embodiment, control apparatus is further operable to: instruct one or more autonomous robots 494 to interact with one or more of the at least one beverage flavoring container 400.

In a further embodiment, each of the at least one beverage flavoring container 400 further comprises a spectral sensor 607 positioned along an interior surface area of each of the at least one beverage flavoring container 400, where the spectral sensor 607 is exposed to the sealable chamber. Spectral sensor 607 is also configured to collect optical properties of at least one of the at least one flavoring agent 305 or the at least one alcoholic beverage 430 to determine a presence and concentration of one or more molecules.

In a further embodiment, the integration workflow of the flow diagram of method 900 further includes sending, via the control apparatus 480, programmable instructions executable by a processor of each of the at least one autonomous robot 494 causes a gripping device of each of the at least one autonomous robot 494 to perform at least one of: picking up a respective one of the at least one container 400, attaching a hose line to a respective one of the inlet orifice 140 and the outlet orifice 145 (see FIG. 1) of a respective one of the at least one container 400, detaching a hose line to a respective one of the inlet orifice 140 and the outlet orifice 145 of a respective one of the at least one container, or replacing one or more of the at least one flavoring agent 305 in a respective one of the at least one retaining device 460.

In a further embodiment, each of the at least one flavoring agent 305 comprises a piece of wood.

In a further embodiment, each of the at least one piece of wood comprises a honeycomb configuration, where the honeycomb configuration is configured to increase surface area exposure of each of the at least one piece of wood to the alcoholic beverage 430. In an additional embodiment, each of the at least one flavoring agent 305 comprises a wood structure having a lattice configuration, where the lattice configuration is configured to increase surface area exposure of each of the at least one flavoring agent 305 to the at least one alcoholic beverage 430.

In an additional embodiment, a computer program product associated with method 900 is presented for regulating an environment of at least one alcoholic beverage 330. The computer program product comprises a computer readable storage medium having program instructions embodied therewith, where the program instructions are executable by a processor 810 to cause the processor 810 to perform a number of steps.

One step includes determining, via each of at least one pressure sensor 386, a voltage signal indicative of a pressure for each of at least one beverage flavoring container 300 storing a respective one of the at least one alcoholic beverage 330, where each of the at least one beverage flavoring container 300 includes at least one retaining device 360 retaining at least one flavoring agent 305 for suspension of the at least one flavoring agent 305 in a respective one of the at least one alcoholic beverage 330.

Another step includes determining, via each of at least one temperature sensor 384, a voltage signal indicative of a temperature for each of the at least one beverage flavoring container 300.

Another step includes sending, via each of the at least one pressure sensor 386 and each of the at least one temperature sensor 384, the pressure voltage signal and the temperature voltage signal for each of the at least one beverage flavoring container 300.

Another step includes receiving, via a control apparatus 380, a setpoint signal indicative of at least one of a desired pressure setpoint or a desired temperature setpoint for each of the at least one beverage flavoring container 300.

Another step includes controlling, via the control apparatus 380, at least one of a pressure regulation signal or a temperature regulation signal for each of the at least one beverage flavoring container 300 such that each of the at least one sent pressure voltage signal and each of the at least one sent temperature voltage signal match a respective one of the at least one received setpoint signal.

In one embodiment, control apparatus 480 is in electrical communication with at least one of a temperature regulation system 495 or a pressure regulation system 496.

In a further embodiment, another step includes converting, via each of the at least one temperature regulation system 495 or the pressure regulation system 496, a respective one of the at least one pressure regulation signal or the temperature regulation signal to at least one environmental output.

In a further embodiment, a respective one of the at least one environmental output comprises a change in temperature to an entirety of the enclosed space 493.

In a further embodiment, control apparatus 480 is further operable to receive a setpoint signal indicative of one desired pressure setpoint and one desired temperature setpoint.

In a further embodiment, control apparatus is further operable to: instruct one or more autonomous robots 494 to interact with one or more of the at least one beverage flavoring containers 400.

In a further embodiment, each of the at least one beverage flavoring container 400 further comprises a spectral sensor 607 positioned along an interior surface area of each of the at least one beverage flavoring container 400, where the spectral sensor 607 is exposed to the sealable chamber. Spectral sensor 607 is also configured to collect optical properties of at least one of the at least one flavoring agent 305 or the at least one alcoholic beverage 430 to determine a presence and concentration of one or more molecules.

In a further embodiment, another step includes sending, via the control apparatus 480, programmable instructions executable by a processor of each of the at least one autonomous robot 494 causes a gripping device of each of the at least one autonomous robot 494 to perform at least one of: picking up a respective one of the at least one container 400, attaching a hose line to a respective one of the inlet orifice 140 and the outlet orifice 145 (see FIG. 1) of a respective one of the at least one container 400, detaching a hose line to a respective one of the inlet orifice 140 and the outlet orifice 145 of a respective one of the at least one container, or replacing one or more of the at least one flavoring agent 305 in a respective one of the at least one retaining device 460.

In a further embodiment, each of the at least one flavoring agent 305 comprises a piece of wood. In a further embodiment, each of the at least one piece of wood comprises a honeycomb configuration, where the honeycomb configuration is configured to increase surface area exposure of each of the at least one piece of wood to the alcoholic beverage 430. In an additional embodiment, each of the at least one flavoring agent 305 comprises a wood structure having a lattice configuration, where the lattice configuration is configured to increase surface area exposure of each of the at least one flavoring agent 305 to the at least one alcoholic beverage 430.

For the purposes of this disclosure, the terms "container" and "beverage flavoring container" may be synonymous.

For the purposes of this disclosure, the terms "memory" and "system memory" may be synonymous.

For the purposes of this disclosure, the terms "controller" and "control apparatus" may be synonymous.

For the purposes of this disclosure, a container of any of the disclosed embodiments is configured to induce an "aging" process of an alcoholic beverage, which, in relation to this application, may be considered a flavoring session. In an embodiment, the aging process is performed between 24 and 48 hours (configured to be more "rapid" than the traditional "aging" process).

For the purposes of this disclosure, the term "flavoring" may be understood as the process of an alcoholic beverage, as disclosed, absorbing molecules from a flavoring agent. This process may also be referred to as "infusion", "diffusion", "aging", and/or "maturation".

It is noted that any of the terms "alcoholic beverage", "distilled alcoholic beverage", or "unflavored alcoholic beverage" may refer to an alcoholic beverage that has not absorbed molecules from a flavoring agent. In an embodiment, an alcoholic beverage may be a distilled alcoholic beverage that is utilized in any of the disclosed systems or methods relative to flavoring an alcoholic beverage. In a further embodiment, an alcoholic beverage may be an undistilled alcoholic beverage that is utilized in any of the disclosed systems or methods relative to flavoring an alcoholic beverage.

It is noted that by virtue of the configuration of any of the disclosed beverage flavoring containers, the "angel's share" (which is the evaporated portion of an alcoholic beverage from a traditional barrel) is eliminated, which saves roughly between 20 to 30 percent of an alcoholic beverage. An additional benefit of this elimination includes a reduction in black mold formation due to the evaporated ethanol in the environment (surrounding the traditional barrel/containers disclosed). It is further noted that because the "angel's share" is eliminated, the processes of flavoring an alcoholic beverage can be considered one or more of an: emissions-free process, an eco-friendly process, a "green" process, a net-zero process, and/or a high fire safety rating process.

It is noted that by virtue of the configuration of the disclosed flavoring agents being wood, a much smaller volume of wood can be utilized to flavor an alcoholic beverage, as opposed to a traditional alcohol aging barrel.

In an embodiment, a flavoring agent 705 (pieces of wood) of any of the disclosed embodiments comprises a plain sawn configuration. By virtue of this configuration, a liquid (an alcoholic beverage) is able to penetrate and flow through the pieces of wood more easily than other cuts of wood such as, for example, quarter sawn. In additional embodiments, a flavoring agent (pieces of wood) of any of the disclosed embodiments comprises any of: a flat sawn configuration, a quarter sawn configuration, a half sawn configuration, a rift sawn configuration, or a live sawn configuration.

In an embodiment, a container body of any of the disclosed embodiments that is filled with an alcoholic beverage may house more than one type of flavoring agent (more than one type of wood pieces). By virtue of this feature, more specific and/or unique flavor profiles can be created within a single alcoholic beverage.

In an embodiment, an alcoholic beverage of any of the disclosed embodiments comprises a liquor, such as, but not limited to: whiskey, brandy, rum, gin, vodka, or tequila. In an additional embodiment, an alcoholic beverage of any of the disclosed embodiments comprises any of liqueurs, wine, beer, sake, mead, or hard cider.

It is noted that a container body of any of the disclosed embodiments can include one or more materials configured to provide certain end characteristics for the container as a whole (when the interior volume of the containers are fully encapsulated). In an embodiment, a container body of any of the disclosed embodiments comprises metal. In further embodiments, a container body of any of the disclosed embodiments comprises stainless steel. In further embodiments, a container body of any of the disclosed embodiments comprises polycarbonate or any other hard plastic. In further embodiments, a container body of any of the disclosed embodiments comprises a material that embodies a density to reduce/limit evaporation and/or leakage (reduced/limited penetration of the material by a gas/liquid when a gas/liquid is fully enclosed within the container body). In further embodiments, a container body of any of the disclosed embodiments comprises a material that is configured to be pressure controlled (withstand an inner volume of gas and/or liquid in the container body during changes in pressure). In further embodiments, a container body of any of the disclosed embodiments comprises a material that is configured to be temperature controlled (withstand heat applied to the container body). In further embodiments, a container body of any of the disclosed embodiments comprises a material that is configured to be substantially corrosion resistant (in regards to what the container is filled with). By virtue of the material configuration, any of the previously disclosed embodiments include a greater fire safety rating than a traditional alcohol aging barrel.

It is noted that when a filter of any of the embodiments disclosed includes a flavoring agent with a lattice structure, the flavoring agent with a lattice structure may be similar to the configuration of flavoring agent 205 but on a smaller scale. Additionally, any orifices relative to the lattice structure may be filled via at least one of wood chips or sawdust.

In an embodiment, a container body of any of the disclosed embodiments comprises a tank structure. In further embodiments, a container body of any of the disclosed embodiments comprises any of an open top tank configuration, a seal tank configuration, or a tank with an unsealed lid.

In any embodiments including a beverage flavoring container and a lid section, a lid section may not extend to a sidewall of a beverage flavoring container and may be smaller than a circumference/perimeter of the beverage flavoring container. As an example, a beverage flavoring container comprises a capacity of 10,000 gallons and includes a lid section having a width of three feet.

In an embodiment, a retaining device of any of the disclosed embodiments is substantially metal. In further embodiments, a retaining device of any of the disclosed embodiments comprises stainless steel.

In an embodiment, an inlet tubing and/or an outlet tubing of any of the disclosed embodiments is substantially metal. In further embodiments, an inlet tubing and/or an outlet tubing of any of the disclosed embodiments comprises stainless steel.

In any of the disclosed embodiments, one of an inlet (orifice) or an outlet (orifice) may be utilized as an inlet (orifice) and an outlet (orifice).

In any of the disclosed embodiments, beverage flavoring containers may be stored on racks similarly to the setup of barrels in a rickhouse. In this case, a lid section or open end may be positioned within a sidewall of a beverage flavoring container.

In any of the disclosed embodiments including a container and one or more filters, any of the filters associated with a container may be positioned in areas within or on the container, where the areas may include one or more of: a lid section of a container, a top (of a lid section or a container), an interior or an exterior side of a container, and/or a bottom of a container.

In any of the disclosed embodiments including at least one of a lid section or a cover portion, the lid section and/or cover portion may be affixed to a respective beverage flavoring container/lid section via any of: a twist-lock mechanism, clips, a push-button disengagement mechanism, threading, a barrel ring (ring compression mechanism), or a tri-clamp.

In any of the disclosed embodiments including at least one of a flavoring agent(s) or a filter(s), the flavoring agent(s) and/or filter(s) may be inserted within a beverage flavoring container prior to adding an alcoholic beverage.

In any of the disclosed embodiments including at least one of a flavoring agent(s) or a filter(s), the flavoring agent(s) and/or filter(s) may be enclosed within a mesh bag.

In any of the disclosed embodiments including at least one of a flavoring agent(s) or a filter(s), the flavoring agent(s) and/or filter(s) may be positioned on a rack within a beverage flavoring container.

In any of the disclosed embodiments including at least one of a flavoring agent(s) or a filter(s), the flavoring agent(s) and/or filter(s) may be removed from a beverage flavoring container via an opening in a bottom section of a beverage flavoring container.

In any of the disclosed embodiments including at least one retaining device each including at least one flavoring agent, the retaining devices may be placed on a bottom section of the beverage flavoring container.

In any of the disclosed embodiments including a container, any portion of a container may comprise a wood structure (including lid sections) in order to allow for natural oxygenation of an alcoholic beverage.

In any of the disclosed embodiments including a flavoring agent comprising some type of wood structure, the wood may comprise one or more of the following types of wood: oak, elm, beech, cherry, chestnut, and/or ash.

In any of the disclosed embodiments including a container, an inert gas may be utilized to increase esterification within an alcoholic beverage (adding to the flavor profile). Inert gases may include, but are not limited to: oxygen or nitrogen.

In any of the disclosed embodiments, air may be purged out of a beverage flavoring container. In further embodiments, air may be purged out of a beverage flavoring container via a vacuum pump.

In any of the disclosed embodiments including a pressure sensor and/or a pressure regulation system, any of the pressure sensor and/or pressure regulation system comprises an analog gauge configured to read pressure measurements.

The example systems, methods, and acts described in the embodiments presented previously are illustrative, and, in alternative embodiments, certain acts can be performed in a different order, in parallel with one another, omitted entirely, and/or combined between different example embodiments, and/or certain additional acts can be performed, without departing from the scope and spirit of various embodiments. Accordingly, such alternative embodiments are included in the description herein.

As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

As used herein, "hardware" can include a combination of discrete components, an integrated circuit, an application-specific integrated circuit, a field programmable gate array, or other suitable hardware. As used herein, "software" can include one or more objects, agents, threads, lines of code, subroutines, separate software applications, two or more lines of code or other suitable software structures operating in two or more software applications, on one or more processors (where a processor includes one or more micro-computers or other suitable data processing units, memory devices, input-output devices, displays, data input devices such as a keyboard or a mouse, peripherals such as printers and speakers, associated drivers, control cards, power sources, network devices, docking station devices, or other suitable devices operating under control of software systems in conjunction with the processor or other devices), or other suitable software structures. In one exemplary embodiment, software can include one or more lines of code or other suitable software structures operating in a general purpose software application, such as an operating system, and one or more lines of code or other suitable software structures operating in a specific purpose software application. As used herein, the term "couple" and its cognate terms, such as "couples" and "coupled," can include a physical connection (such as a copper conductor), a virtual connection (such as through randomly assigned memory locations of a data memory device), a logical connection (such as through logical gates of a semiconducting device), other suitable connections, or a suitable combination of such connections. The term "data" can refer to a suitable structure for using, conveying or storing data, such as a data field, a data buffer, a data message having the data value and sender/receiver address data, a control message having the data value and one or more operators that cause the receiving system or component to perform a function using the data, or other suitable hardware or software components for the electronic processing of data.

In general, a software system is a system that operates on a processor to perform predetermined functions in response to predetermined data fields. For example, a system can be defined by the function it performs and the data fields that it performs the function on. As used herein, a NAME system, where NAME is typically the name of the general function that is performed by the system, refers to a software system that is configured to operate on a processor and to perform the disclosed function on the disclosed data fields. Unless a specific algorithm is disclosed, then any suitable algorithm that would be known to one of skill in the art for performing the function using the associated data fields is contemplated as falling within the scope of the disclosure. For example, a message system that generates a message that includes a sender address field, a recipient address field and a message field would encompass software operating on a processor that can obtain the sender address field, recipient address field and message field from a suitable system or device of the processor, such as a buffer device or buffer system, can assemble the sender address field, recipient address field and message field into a suitable electronic message format (such as an electronic mail message, a TCP/IP message or any other suitable message format that has a sender address field, a recipient address field and message field), and can transmit the electronic message using electronic messaging systems and devices of the processor over a communications medium, such as a network. One of ordinary skill in the art would be able to provide the specific coding for a specific application based on the foregoing disclosure, which is intended to set forth exemplary embodiments of the present disclosure, and not to provide a tutorial for someone having less than ordinary skill in the art, such as someone who is unfamiliar with programming or processors in a suitable programming language. A specific algorithm for performing a function can be provided in a flow chart form or in other suitable formats, where the data fields and associated functions can be set forth in an exemplary order of operations, where the order can be rearranged as suitable and is not intended to be limiting unless explicitly stated to be limiting.

The above-disclosed embodiments have been presented for purposes of illustration and to enable one of ordinary skill in the art to practice the disclosure, but the disclosure is not intended to be exhaustive or limited to the forms disclosed. Many insubstantial modifications and variations will be apparent to those of ordinary skill in the art without departing from the scope and spirit of the disclosure. The scope of the claims is intended to broadly cover the disclosed embodiments and any such modification. Further, the following clauses represent additional embodiments of the disclosure and should be considered within the scope of the disclosure:

Clause 1, a computer-implemented method of training a machine learning model for evaluating flavor profiles of an alcoholic beverage, the method comprising: for each of a plurality of flavoring sessions: collecting, via a spectral sensor, optical properties of at least one of the alcoholic beverage within a container or at least one flavoring agent suspended in the alcoholic beverage; collecting, by at least one of a temperature sensor or a pressure sensor, environment data of the container during the flavoring session; upon completion of the flavoring session, displaying, via a control apparatus, a user interface requesting a human taste tester to select one or more labels for the completed flavoring session, wherein the human taste tester selects the one or more labels using the user interface; storing, via a memory of the control apparatus, the selected labels responsive to the selection of the human taste tester, and extracting, via a feature extraction module, features from the optical properties and the environment data based on predetermined criteria, the extracted features including some of the optical properties and some of the environment data collected at different points in time during the flavoring session; and training, via a machine learning engine, a machine learning model to continuously learn flavor characteristics under the plurality of flavoring sessions using the extracted features and the one or more labels selected by the human taste tester for the plurality of flavoring sessions; wherein the trained machine learning model is deployed for quality control of the alcoholic beverage and for determining the difference between a good batch of the alcoholic beverage and a poor batch of the alcoholic beverage.

Clause 2, the method of Clause 1, wherein the collected optical properties of the alcoholic beverage within the container and the at least one flavoring agent suspended in the alcoholic beverage determine at least one of: a presence of one or more molecules, a concentration of one or more molecules, or a color of the alcoholic beverage.

Clause 3, the method of Clause 1, wherein, for each flavoring session, the extracted features include one or more of: temperature datapoints, pressure datapoints, at least one of refractive index data or extinction index data relative to at least one of the at least one flavoring agent or the alcoholic beverage, or a timestamp associated with any of the temperature datapoints, the pressure datapoints, or the at least one of the refractive index data or the extinction index data.

Clause 4, the method of Clause 1, wherein the machine learning model is further trained with a database, wherein the database includes information relative to at least one of: alcohol characteristics or wood characteristics.

Clause 5, the method of Clause 1, wherein each of the at least one flavoring agent comprises a wood structure having a lattice configuration, the lattice configuration configured to increase surface area exposure of each of the at least one flavoring agent to the alcoholic beverage.

Clause 6, a system for training a machine learning model for evaluating flavor profiles of an alcoholic beverage, the system comprising: a processor; and a memory coupled to the processor to store instructions, the instructions, when executed by the processor, cause the processor to perform operations, the operations including: for each of a plurality of flavoring sessions: collecting, via a spectral sensor, optical properties of at least one of the alcoholic beverage within a container or at least one flavoring agent suspended in the alcoholic beverage; collecting, by at least one of a temperature sensor or a pressure sensor, environment data of the container during the flavoring session; upon completion of the flavoring session, displaying, via a control apparatus, a user interface requesting a human taste tester to select one or more labels for the completed flavoring session, wherein the human taste tester selects the one or more labels using the user interface; storing, via a memory of the control apparatus, the selected labels responsive to the selection of the human taste tester, and extracting, via a feature extraction module, features from the optical properties and the environment data based on predetermined criteria, the extracted features including some of the optical properties and some of the environment data collected at different points in time during the flavoring session; and training, via a machine learning engine, a machine learning model to continuously learn flavor characteristics under the plurality of flavoring sessions using the extracted features and the one or more labels selected by the human taste tester for the plurality of flavoring sessions; wherein the trained machine learning model is deployed for quality control of the alcoholic beverage and for determining the difference between a good batch of the alcoholic beverage and a poor batch of the alcoholic beverage.

Clause 7, the system of Clause 6, wherein the collected optical properties of the alcoholic beverage within the container and the at least one flavoring agent suspended in the alcoholic beverage determine at least one of: a presence of one or more molecules, a concentration of one or more molecules, or a color of the alcoholic beverage.

Clause 8, the system of Clause 6, wherein, for each flavoring session, the extracted features include: temperature datapoints, pressure datapoints, at least one of refractive index data or extinction index data relative to at least one of the at least one flavoring agent or the alcoholic beverage, and a timestamp associated with each of the temperature datapoints, the pressure datapoints, and the at least one of the refractive index data or the extinction index data.

Clause 9, the system of Clause 6, wherein the machine learning model is further trained with a database, wherein the database includes information relative to at least one of: alcohol characteristics or wood characteristics.

Clause 10, the system of Clause 6, wherein each of the at least one flavoring agent comprises a wood structure having a lattice configuration, the lattice configuration configured to increase surface area exposure of each of the at least one flavoring agent to the alcoholic beverage.

Clause 11, a computer program product for training a machine learning model for evaluating flavor profiles of an alcoholic beverage, the computer program product comprising a computer readable storage medium having program instructions embodied therewith, the program instructions executable by a processor to cause the processor to perform: for each of a plurality of flavoring sessions: collecting, via a spectral sensor, optical properties of at least one of the alcoholic beverage within a container or at least one flavoring agent suspended in the alcoholic beverage; collecting, by at least one of a temperature sensor or a pressure sensor, environment data of the container during the flavoring session; upon completion of the flavoring session, displaying, via a control apparatus, a user interface requesting a human taste tester to select one or more labels for the completed flavoring session, wherein the human taste tester selects the one or more labels using the user interface; storing, via a memory of the control apparatus, the selected labels responsive to the selection of the human taste tester, and extracting, via a feature extraction module, features from the optical properties and the environment data based on predetermined criteria, the extracted features including some of the optical properties and some of the environment data collected at different points in time during the flavoring session; and training, via a machine learning engine, a machine learning model to continuously learn flavor characteristics under the plurality of flavoring sessions using the extracted features and the one or more labels selected by the human taste tester for the plurality of flavoring sessions; wherein the trained machine learning model is deployed for quality control of the alcoholic beverage and for determining the difference between a good batch of the alcoholic beverage and a poor batch of the alcoholic beverage.

Clause 12, the computer program product of Clause 11, wherein the collected optical properties of the alcoholic beverage within the container and the at least one flavoring agent suspended in the alcoholic beverage determine at least one of: a presence of one or more molecules, a concentration of one or more molecules, or a color of the alcoholic beverage.

Clause 13, the computer program product of Clause 11, wherein, for each flavoring session, the extracted features include: temperature datapoints, pressure datapoints, at least one of refractive index data or extinction index data relative to at least one of the at least one flavoring agent or the alcoholic beverage, and a timestamp associated with each of the temperature datapoints, the pressure datapoints, and the at least one of the refractive index data or the extinction index data.

Clause 14, the computer program product of Clause 11, wherein the machine learning model is further trained with a database, wherein the database includes information relative to at least one of: alcohol characteristics or wood characteristics.

Clause 15, the computer program product of Clause 11, wherein each of the at least one flavoring agent comprises a wood structure having a lattice configuration, the lattice configuration configured to increase surface area exposure of each of the at least one flavoring agent to the alcoholic beverage.

What is claimed is:

1. A computer-implemented method of training a machine learning model for evaluating flavor profiles of an alcoholic beverage, the method comprising:

for each of a plurality of flavoring sessions:

collecting, via a spectral sensor, optical properties of at least one of the alcoholic beverage within a container or at least one flavoring agent suspended in the alcoholic beverage;

collecting, by at least one of a temperature sensor or a pressure sensor, environment data of the container during the flavoring session;

upon completion of the flavoring session, displaying, via a control apparatus, a user interface requesting a human taste tester to select one or more labels for the completed flavoring session, wherein the human taste tester selects the one or more labels using the user interface;

storing, via a memory of the control apparatus, the selected labels responsive to the selection of the human taste tester, and extracting, via a feature extraction module, features from the optical properties and the environment data based on predetermined criteria, the extracted features including some of the optical properties and some of the environment data collected at different points in time during the flavoring session; and training, via a machine learning engine, a machine learning model to continuously learn flavor characteristics under the plurality of flavoring sessions using the extracted features and the one or more labels selected by the human taste tester for the plurality of flavoring sessions;

wherein the trained machine learning model is deployed for quality control of the alcoholic beverage and for determining the difference between a good batch of the alcoholic beverage and a poor batch of the alcoholic beverage.

2. The method of claim 1, wherein the collected optical properties of the alcoholic beverage within the container and the at least one flavoring agent suspended in the alcoholic beverage determine at least one of: a presence of one or more molecules, a concentration of one or more molecules, or a color of the alcoholic beverage.

3. The method of claim 1, wherein, for each flavoring session, the extracted features include one or more of: temperature datapoints, pressure datapoints, at least one of refractive index data or extinction index data relative to at least one of the at least one flavoring agent or the alcoholic beverage, or a timestamp associated with any of the temperature datapoints, the pressure datapoints, or the at least one of the refractive index data or the extinction index data.

4. The method of claim 1, wherein the machine learning model is further trained with a database, wherein the database includes information relative to at least one of: alcohol characteristics or wood characteristics.

5. The method of claim 1, wherein each of the at least one flavoring agent comprises a wood structure having a lattice configuration, the lattice configuration configured to increase surface area exposure of each of the at least one flavoring agent to the alcoholic beverage.

6. A system for training a machine learning model for evaluating flavor profiles of an alcoholic beverage, the system comprising:

a processor; and a memory coupled to the processor to store instructions, the instructions, when executed by the processor, cause the processor to perform operations, the operations including:

for each of a plurality of flavoring sessions:

collecting, via a spectral sensor, optical properties of at least one of the alcoholic beverage within a container or at least one flavoring agent suspended in the alcoholic beverage;

collecting, by at least one of a temperature sensor or a pressure sensor, environment data of the container during the flavoring session;

upon completion of the flavoring session, displaying, via a control apparatus, a user interface requesting a human taste tester to select one or more labels for the completed flavoring session, wherein the human taste tester selects the one or more labels using the user interface;

storing, via a memory of the control apparatus, the selected labels responsive to the selection of the human taste tester, and extracting, via a feature extraction module, features from the optical properties and the environment data based on predetermined criteria, the extracted features including some of the optical properties and some of the environment data collected at different points in time during the flavoring session; and training, via a machine learning engine, a machine learning model to continuously learn flavor characteristics under the plurality of flavoring sessions using the extracted features and the one or more labels selected by the human taste tester for the plurality of flavoring sessions;

wherein the trained machine learning model is deployed for quality control of the alcoholic beverage and for determining the difference between a good batch of the alcoholic beverage and a poor batch of the alcoholic beverage.

7. The system of claim 6, wherein the collected optical properties of the alcoholic beverage within the container and the at least one flavoring agent suspended in the alcoholic beverage determine at least one of: a presence of one or more molecules, a concentration of one or more molecules, or a color of the alcoholic beverage.

8. The system of claim 6, wherein, for each flavoring session, the extracted features include: temperature datapoints, pressure datapoints, at least one of refractive index data or extinction index data relative to at least one of the at least one flavoring agent or the alcoholic beverage, and a timestamp associated with each of the temperature datapoints, the pressure datapoints, and the at least one of the refractive index data or the extinction index data.

9. The system of claim 6, wherein the machine learning model is further trained with a database, wherein the database includes information relative to at least one of: alcohol characteristics or wood characteristics.

10. The system of claim 6, wherein each of the at least one flavoring agent comprises a wood structure having a lattice configuration, the lattice configuration configured to increase surface area exposure of each of the at least one flavoring agent to the alcoholic beverage.

11. A computer program product for training a machine learning model for evaluating flavor profiles of an alcoholic beverage, the computer program product comprising a computer readable storage medium having program instructions embodied therewith, the program instructions executable by a processor to cause the processor to perform:

for each of a plurality of flavoring sessions:

collecting, via a spectral sensor, optical properties of at least one of the alcoholic beverage within a container or at least one flavoring agent suspended in the alcoholic beverage;

collecting, by at least one of a temperature sensor or a pressure sensor, environment data of the container during the flavoring session;

upon completion of the flavoring session, displaying, via a control apparatus, a user interface requesting a human taste tester to select one or more labels for the completed flavoring session, wherein the human taste tester selects the one or more labels using the user interface;

storing, via a memory of the control apparatus, the selected labels responsive to the selection of the human taste tester, and extracting, via a feature extraction module, features from the optical properties and the environment data based on predetermined criteria, the extracted features including some of the optical properties and some of the environment data collected at different points in time during the flavoring session; and training, via a machine learning engine, a machine learning model to continuously learn flavor characteristics under the plurality of flavoring sessions using the extracted features and the one or more labels selected by the human taste tester for the plurality of flavoring sessions;

wherein the trained machine learning model is deployed for quality control of the alcoholic beverage and for determining the difference between a good batch of the alcoholic beverage and a poor batch of the alcoholic beverage.

12. The computer program product of claim 11, wherein the collected optical properties of the alcoholic beverage within the container and the at least one flavoring agent suspended in the alcoholic beverage determine at least one of: a presence of one or more molecules, a concentration of one or more molecules, or a color of the alcoholic beverage.

13. The computer program product of claim 11, wherein, for each flavoring session, the extracted features include: temperature datapoints, pressure datapoints, at least one of refractive index data or extinction index data relative to at least one of the at least one flavoring agent or the alcoholic beverage, and a timestamp associated with each of the temperature datapoints, the pressure datapoints, and the at least one of the refractive index data or the extinction index data.

14. The computer program product of claim 11, wherein the machine learning model is further trained with a database, wherein the database includes information relative to at least one of: alcohol characteristics or wood characteristics.

15. The computer program product of claim 11, wherein each of the at least one flavoring agent comprises a wood structure having a lattice configuration, the lattice configuration configured to increase surface area exposure of each of the at least one flavoring agent to the alcoholic beverage.

* * * * *